(12) United States Patent
Gartstein et al.

(10) Patent No.: US 7,578,954 B2
(45) Date of Patent: Aug. 25, 2009

(54) METHOD FOR MANUFACTURING MICROSTRUCTURES HAVING MULTIPLE MICROELEMENTS WITH THROUGH-HOLES

(75) Inventors: Vladimir Gartstein, Cincinnati, OH (US); Faiz Feisal Sherman, West Chester, OH (US)

(73) Assignee: Corium International, Inc., Menlo Park, CA (US)

( * ) Notice: Subject to any disclaimer, the term of this patent is extended or adjusted under 35 U.S.C. 154(b) by 114 days.

(21) Appl. No.: 10/373,251

(22) Filed: Feb. 24, 2003

(65) Prior Publication Data

US 2004/0164454 A1  Aug. 26, 2004

(51) Int. Cl.
*B29C 43/02* (2006.01)
*B29C 1/48* (2006.01)

(52) U.S. Cl. ...................... 264/154; 264/319

(58) Field of Classification Search ........................ None
See application file for complete search history.

(56) References Cited

U.S. PATENT DOCUMENTS

| | | | |
|---|---|---|---|
| 3,918,449 A | 11/1975 | Pistor | |
| 3,964,482 A | 6/1976 | Gerstel et al. | |
| 4,055,029 A | 10/1977 | Kalbow | |
| 4,180,232 A | 12/1979 | Hardigg | |
| 4,381,963 A | 5/1983 | Goldstein et al. | |
| 4,585,991 A | 4/1986 | Reid et al. | |
| 4,784,737 A | 11/1988 | Ray et al. | |
| 4,837,049 A | 6/1989 | Byers et al. | |
| 5,134,079 A | 7/1992 | Cusack et al. | |
| 5,156,591 A | 10/1992 | Gross et al. | |
| 5,158,073 A | 10/1992 | Bukowski | |
| 5,162,043 A | 11/1992 | Lew et al. | |
| 5,198,192 A | 3/1993 | Saito et al. | |
| 5,215,088 A | 6/1993 | Normann et al. | |
| 5,244,711 A * | 9/1993 | Drelich et al. | ............... 428/113 |
| 5,250,023 A | 10/1993 | Lee et al. | |
| 5,250,067 A | 10/1993 | Gelfer et al. | |
| 5,256,360 A | 10/1993 | Li | |

(Continued)

FOREIGN PATENT DOCUMENTS

DE          23 19 591          11/1974

(Continued)

OTHER PUBLICATIONS

McAllister, H., "Micromachined Microneedles for Transdermal Drug Delivery", Allen & Prausnitz, Georgia Institute of Technology, Atlanta, GA.

(Continued)

*Primary Examiner*—Monica A Huson
(74) *Attorney, Agent, or Firm*—Mintz, Levin, Cohn, Ferris, Glovsky and Popeo, PC

(57) ABSTRACT

A method is provided for manufacturing microstructures of the type which contain a substrate and an array of protruding microelements with through-holes, which are used in penetrating layers of skin. The microelements are embossed or pressed into an initial substrate structure, which in some embodiments is formed from extruded polymeric material, and in some cases from two layers of polymer that are co-extruded. The through-holes are formed from filled through-cylinders of a second material that is removed after the embossing or pressing step; in other instances, the through-holes are left hollow during the embossing or pressing step.

10 Claims, 13 Drawing Sheets

U.S. PATENT DOCUMENTS

| | | |
|---|---|---|
| 5,279,544 A | 1/1994 | Gross et al. |
| 5,318,557 A | 6/1994 | Gross |
| 5,320,600 A | 6/1994 | Lambert |
| 5,362,307 A | 11/1994 | Guy et al. |
| 5,383,512 A | 1/1995 | Jarvis |
| 5,487,726 A | 1/1996 | Rabineau et al. |
| 5,498,235 A | 3/1996 | Flower |
| 5,512,219 A | 4/1996 | Rowland et al. |
| 5,527,288 A | 6/1996 | Gross et al. |
| 5,531,675 A | 7/1996 | Yoo |
| 5,536,263 A | 7/1996 | Rolf et al. |
| 5,551,953 A | 9/1996 | Lattin et al. |
| 5,567,376 A | 10/1996 | Turi et al. |
| 5,591,123 A | 1/1997 | Sibalis et al. |
| 5,591,139 A | 1/1997 | Lin et al. |
| 5,611,806 A | 3/1997 | Jang |
| 5,645,977 A | 7/1997 | Wu et al. |
| 5,658,515 A | 8/1997 | Lee et al. |
| 5,676,850 A | 10/1997 | Reed et al. |
| 5,681,580 A | 10/1997 | Jang et al. |
| 5,697,901 A | 12/1997 | Ericksson |
| 5,704,520 A | 1/1998 | Gross |
| 5,711,761 A | 1/1998 | Untereker et al. |
| 5,728,089 A | 3/1998 | Lal et al. |
| 5,730,714 A | 3/1998 | Guy et al. |
| 5,735,273 A | 4/1998 | Kurnik et al. |
| 5,771,890 A | 6/1998 | Tamada |
| 5,800,420 A | 9/1998 | Gross et al. |
| 5,807,375 A | 9/1998 | Gross et al. |
| 5,814,020 A | 9/1998 | Gross |
| 5,820,622 A | 10/1998 | Gross et al. |
| 5,827,183 A | 10/1998 | Kurnik et al. |
| 5,848,985 A | 12/1998 | Muroki |
| 5,848,990 A | 12/1998 | Cirelli et al. |
| 5,848,991 A | 12/1998 | Gross et al. |
| 5,855,801 A | 1/1999 | Lin et al. |
| 5,873,849 A | 2/1999 | Bernard |
| 5,879,326 A | 3/1999 | Godshall et al. |
| 5,938,684 A | 8/1999 | Lynch et al. |
| 5,948,488 A | 9/1999 | Marecki et al. |
| 5,964,729 A | 10/1999 | Choi et al. |
| 5,983,136 A | 11/1999 | Kamen |
| 5,997,986 A * | 12/1999 | Turi et al. ................... 428/138 |
| 6,014,584 A | 1/2000 | Hofmann et al. |
| 6,023,629 A | 2/2000 | Tamada |
| 6,024,553 A | 2/2000 | Shimalla |
| 6,036,659 A | 3/2000 | Ray et al. |
| 6,038,465 A | 3/2000 | Melton, Jr. |
| 6,047,208 A | 4/2000 | Flower |
| 6,050,988 A | 4/2000 | Zuck |
| 6,055,453 A | 4/2000 | Hofmann et al. |
| 6,083,196 A | 7/2000 | Trautman et al. |
| 6,091,975 A | 7/2000 | Daddona et al. |
| 6,106,751 A | 8/2000 | Talbot et al. |
| 6,129,696 A | 10/2000 | Sibalis |
| 6,132,755 A | 10/2000 | Eicher et al. |
| 6,135,990 A | 10/2000 | Heller et al. |
| 6,183,434 B1 | 2/2001 | Eppstein |
| 6,216,034 B1 | 4/2001 | Hofmann et al. |
| 6,219,574 B1 | 4/2001 | Cormier et al. |
| 6,230,051 B1 | 5/2001 | Cormier et al. |
| 6,241,701 B1 | 6/2001 | Hofmann |
| 6,256,533 B1 | 7/2001 | Yuzhakov et al. |
| 6,312,612 B1 | 11/2001 | Sherman et al. |
| 6,322,808 B1 | 11/2001 | Trautman et al. |
| 6,334,856 B1 | 1/2002 | Allen et al. |
| 6,355,054 B1 | 3/2002 | Neuberger |
| 6,375,627 B1 | 4/2002 | Mauze et al. |
| 6,379,324 B1 | 4/2002 | Gartstein et al. |
| 6,440,096 B1 | 8/2002 | Lastovich et al. |
| 6,451,240 B1 | 9/2002 | Sherman et al. |
| 6,461,716 B1 | 10/2002 | Lee et al. |
| 6,471,903 B2 | 10/2002 | Sherman et al. |
| 6,476,288 B1 | 11/2002 | VanRijswijck et al. |
| 6,494,830 B1 | 12/2002 | Wessel |
| 6,503,231 B1 | 1/2003 | Prausnitz et al. |
| 6,511,463 B1 | 1/2003 | Wood et al. |
| 6,532,386 B2 | 3/2003 | Sun et al. |
| 6,533,884 B1 | 3/2003 | Mallik |
| 6,537,242 B1 | 3/2003 | Palmer |
| 6,558,361 B1 | 5/2003 | Yeshurun |
| 6,562,014 B2 | 5/2003 | Lin et al. |
| 6,565,532 B1 | 5/2003 | Yuzhakov et al. |
| 6,591,124 B2 | 7/2003 | Sherman et al. |
| 6,591,133 B1 | 7/2003 | Joshi |
| 6,611,706 B2 | 8/2003 | Avrahami et al. |
| 6,611,707 B1 | 8/2003 | Prausnitz et al. |
| 6,623,457 B1 | 9/2003 | Rosenberg |
| 6,629,949 B1 | 10/2003 | Douglas |
| 6,689,103 B1 | 2/2004 | Palasis |
| 6,743,211 B1 | 6/2004 | Prausnitz et al. |
| 6,767,341 B2 | 7/2004 | Cho |
| 6,770,480 B1 | 8/2004 | Canham |
| 6,778,853 B1 | 8/2004 | Heller et al. |
| 6,780,171 B2 | 8/2004 | Gabel et al. |
| 6,835,184 B1 | 12/2004 | Sage et al. |
| 6,881,203 B2 | 4/2005 | Delmore et al. |
| 6,945,952 B2 | 9/2005 | Kwon et al. |
| 2001/0023324 A1 | 9/2001 | Pronovost et al. |
| 2002/0006355 A1 | 1/2002 | Whitson |
| 2002/0032415 A1 | 3/2002 | Trautman et al. |
| 2002/0042589 A1 | 4/2002 | Marsoner |
| 2002/0045859 A1 | 4/2002 | Gartstein et al. |
| 2002/0045907 A1 | 4/2002 | Sherman et al. |
| 2002/0082543 A1 | 6/2002 | Park et al. |
| 2002/0133129 A1 | 9/2002 | Arias et al. |
| 2002/0138049 A1 | 9/2002 | Allen et al. |
| 2002/0177839 A1 | 11/2002 | Cormier et al. |
| 2002/0177858 A1 | 11/2002 | Sherman et al. |
| 2002/0188245 A1 | 12/2002 | Martin et al. |
| 2002/0193729 A1 | 12/2002 | Cormier et al. |
| 2003/0093028 A1 | 5/2003 | Spiegel |
| 2003/0135167 A1 | 7/2003 | Gonnelli |
| 2003/0199810 A1 | 10/2003 | Trautman et al. |
| 2003/0199812 A1 | 10/2003 | Rosenberg |
| 2003/0208138 A1 | 11/2003 | Olson |
| 2003/0208167 A1 | 11/2003 | Prausnitz et al. |
| 2003/0212397 A1 | 11/2003 | Avrahami et al. |
| 2004/0096455 A1 | 5/2004 | Maa et al. |
| 2004/0143211 A1 | 7/2004 | Haider et al. |
| 2004/0181203 A1 | 9/2004 | Cormier et al. |
| 2004/0204669 A1 | 10/2004 | Hofmann |
| 2004/0236271 A1 | 11/2004 | Theeuwes et al. |

FOREIGN PATENT DOCUMENTS

| | | |
|---|---|---|
| DE | 196 24 578 A1 | 1/1998 |
| EP | 0 301 599 A2 | 2/1989 |
| EP | 0 312 662 A1 | 4/1989 |
| EP | 0 407 063 A1 | 1/1991 |
| EP | 1 086 719 A1 | 3/2001 |
| EP | 1 174 078 A2 | 1/2002 |
| FR | 2535602 | 5/1984 |
| GB | 783479 | 9/1957 |
| GB | 2221394 A | 2/1990 |
| JP | 09-051878 | 2/1997 |
| SU | 1 667 864 | 8/1991 |
| WO | WO 93/17754 A1 | 9/1993 |
| WO | WO 94/23777 A1 | 10/1994 |
| WO | WO 95/22612 A2 | 8/1995 |
| WO | WO 96/00109 A1 | 1/1996 |
| WO | WO 96/17648 A1 | 6/1996 |
| WO | WO 96/37155 A1 | 11/1996 |
| WO | WO 96/37256 A1 | 11/1996 |

| | | |
|---|---|---|
| WO | WO 97/03718 A1 | 2/1997 |
| WO | WO 97/48440 A1 | 12/1997 |
| WO | WO 97/48441 A1 | 12/1997 |
| WO | WO 97/48442 A1 | 12/1997 |
| WO | WO 98/00193 A1 | 1/1998 |
| WO | WO 99/00155 A1 | 1/1999 |
| WO | WO 99/29298 A2 | 6/1999 |
| WO | WO 99/29364 A1 | 6/1999 |
| WO | WO 99/29365 A1 | 6/1999 |
| WO | WO 99/64580 A1 | 12/1999 |
| WO | WO 00/05166 A1 | 2/2000 |
| WO | WO 00/35530 A1 | 6/2000 |
| WO | WO 00/74763 A2 | 12/2000 |
| WO | WO 00/74765 A1 | 12/2000 |
| WO | WO 00/74766 A1 | 12/2000 |
| WO | WO 02/07813 A1 | 1/2002 |
| WO | WO 02/32331 A2 | 4/2002 |
| WO | WO 02/072189 A2 | 9/2002 |
| WO | WO 03/024290 A1 | 3/2003 |
| WO | WO 03/024518 A2 | 3/2003 |

OTHER PUBLICATIONS

Sebastian, H. et al., "Microfabricated Microneedles: A Novel Approach to Transdermal Drug Delivery", Journal of Pharmaceutical Sciences, Aug. 1998, pp. 922-925, vol. 87, No. 8, Atlanta, GA.

Chun, K. et al., An Array of Hollow Microcapillaries for the Controlled Injection of Genetic Materials into Animal/Plat Cells, The University of Tokyo.

Wouters, S. et al., "Microelectrochemical Systems for Drug Delivery", Electrochimica Acta., 1997, pp. 3385-3390, vol. 42, Nos. 20-22.

Prausnitz, M. R., et al., "Transdermal Delivery of Macromolecules: Recent Advances by Modification of Skin's Barrier Properties", Therapeutic Protein and Peptide Formulation and Delivery, pp. 124-153, Chapter 8, ACS Symposium Series 675, Georgia Institute of Technology.

Prausnitz, M. R., et al., Transdermal Transport Efficiency During Skin Electroporation and Iontophoresis, Journal of Controlled Release 38, 1996, pp. 205-217, Massachusetts Institute of Technology, Cambridge, MA.

Papautsky, I. E., et al., "Micromachined Pipette Arrays (MPA)", pp. 2281-2284, Proceedings—19$^{th}$ International Conference—IEEE/EMBS Oct. 30-Nov. 2, 1997, Chicago, IL.

* cited by examiner

METHOD FOR MANUFACTURING MICROSTRUCTURES HAVING MULTIPLE MICROELEMENTS WITH THROUGH-HOLES

TECHNICAL FIELD

The present invention relates generally to manufacturing microstructures and is particularly directed to microstructures of the type which contain a substrate and an array of protruding microelements with through-holes. The invention is specifically disclosed as methods for constructing microstructures that can penetrate skin layers, in which the microelements are embossed or pressed into the initial substrate structure, which in some is embodiments is formed from extruded polymeric material, and in some cases two layers of polymer that are co-extruded. The through-holes are formed in some embodiments from filled through-cylinders of a second material that is removed after the embossing or pressing step; in other embodiments, the through-holes are left hollow during the embossing or pressing step.

BACKGROUND OF THE INVENTION

Microstructures containing an array of microelements have been disclosed in various patent publications, many of which include openings that allow a fluid exchange between the top and bottom surfaces of the microelement array. The individual microelements typically are designed to penetrate the stratum corneum of animal skin, or to penetrate some other type of membrane. Once the penetration has been accomplished, a fluid (e.g., liquid drugs) can be dispensed into the body from a reservoir in the microstructure, or in the reverse direction, a body fluid can be sampled into such a reservoir in the microstructure.

The proper size and shape of the microelements depends upon many factors, and for some applications (e.g., drug delivery or body fluid sampling through human skin), several different sizes, and especially shapes, will suffice. Some applications of microstructures do not require through-openings; however, for those applications that do need through-openings, it is important to find a way to manufacture such microstructures in an inexpensive (and high-volume) manner, within tolerable accuracy to lower reject rates during the manufacturing of these devices.

Various sizes and shapes of microstructures have been disclosed by the present inventors, in commonly assigned United States patent applications, as noted below. The documents listed below are incorporated herein by reference, in their entirety: INTRACUTANEOUS MICRONEEDLE ARRAY APPARATUS, Ser. No. 09/328,947, filed on Jun. 9, 1999; APPARATUS AND METHOD FOR USING AN INTRACUTANEOUS MICRONEEDLE ARRAY, Ser. No. 09/329,025, filed on Jun. 9, 1999, now U.S. Pat. No. 6,256,533 B1, which issued Jul. 3, 2001; APPARATUS AND METHOD FOR MANUFACTURING AN INTRACUTANEOUS MICRONEEDLE ARRAY, Ser. No. 09/328,946, filed on Jun. 9, 1999, now U.S. Pat. No. 6,312,612 B1, which issued Nov. 6, 2001; INTRACUTANEOUS EDGED MICRONEEDLE APPARATUS, Ser. No. 09/580,780, filed on May 26, 2000; INTRACUTANEOUS MICRONEEDLE ARRAY APPARATUS, Ser. No. 09/580,819, filed on May 26, 2000; METHOD OF MANUFACTURING AN INTRACUTANEOUS MICRONEEDLE ARRAY, Ser. No. 09/579,798, filed on May 26, 2000; METHOD OF MANUFACTURING MICRONEEDLE STRUCTURES USING SOFT LITHOGRAPHY AND PHOTOLITHOGRAPHY, Ser. No. 09/808,534, filed on Mar. 14, 2001; MICROSTRUCTURES FOR TREATING AND CONDITIONING SKIN, Ser. No. 09/952,403, filed on Sep. 14, 2001; MICROSTRUCTURES FOR DELIVERING A COMPOSITION CUTANEOUSLY TO SKIN, Ser. No. 09/952,391, filed on Sep. 14, 2001; MICROSTRUCTURES FOR DELIVERING A COMPOSITION CUTANEOUSLY TO SKIN USING ROTATABLE STRUCTURES, Ser. No. 10/216,148, filed on Aug. 9, 2002.

It would be beneficial to provide an improved method of manufacturing microstructures with openings that extend through the substrate and through the individual microelements, and to do so in a high-volume, low-cost manner. It would also be beneficial to provide a method manufacturing such microstructures in a way that ensures most, or all, of the microelements contains at least one such through-hole within the microelements' perimeter.

SUMMARY OF THE INVENTION

Accordingly, it is an advantage of the present invention to provide a methodology for forming a microstructure having an array of microelements with openings therethrough, in which the microstructure can be formed with a well-aligned two-polymer system using an embossing or molding procedure.

It is another advantage of the present invention to provide a methodology for forming a microstructure having an array of microelements with openings therethrough, in which the microstructure can be formed with a well-aligned two-polymer system using an embossing or molding procedure, in which the microelements are formed in a co-extrusion process.

It is yet another advantage of the present invention to provide a methodology for forming a microstructure having an array of microelements with openings therethrough, in which the microstructure can be formed with a semi-random hole location two-polymer system using an embossing or molding procedure.

It is still another advantage of the present invention to provide a methodology for forming a microstructure having an array of microelements with openings therethrough, in which the microstructure can be formed with a well-aligned two-polymer system using an embossing or molding procedure, in which the microelements are formed in a co-extrusion process and the holes are located in a semi-random manner.

It is a further advantage of the present invention to provide a method of manufacture of microstructures that uses an embossing or molding process to form through-holes in individual microelements, either as a well-aligned set of holes or in which the holes are located in a semi-random manner.

It is yet a further advantage of the present invention to provide a methodology for forming a microstructure having an array of microelements that uses a mask plate and high pressure liquid or gas jets to form through-holes in the microelements.

It is a yet further advantage of the present invention to provide a methodology for forming a microstructure having an array of microelements using a heated plate to produce through-holes in the microelements.

It is still a further advantage of the present invention to provide a methodology for forming microstructures of individual microelements in which two die-halves or mold-halves are provided to form individual microelements with through-holes, in which the die/mold-halves are somewhat self-aligning.

Additional advantages and other novel features of the invention will be set forth in part in the description that follows and in part will become apparent to those skilled in the art upon examination of the following or may be learned with the practice of the invention.

To achieve the foregoing and other advantages, and in accordance with one aspect of the present invention, a method for constructing a microstructure is provided, in which the method comprises the following steps: providing a substrate of a first material, the substrate having a first substantially planar surface and a second substantially planar surface opposite the first surface, the substrate having a plurality of openings formed between the first and second surfaces; and pressing against the first surface of the substrate of material with an object having a predetermined shape to thereby form a plurality of microelement protrusions in the first surface, the plurality of microelement protrusions being of at least one predetermined shape and size, each of the plurality of microelement protrusions having a base-shape that forms a perimeter along the first surface; wherein at least one of the plurality of microelement protrusions exhibit at least one of the plurality of openings within their the perimeter.

In accordance with another aspect of the present invention, a method for constructing a microstructure is provided, in which the method comprises the following steps: providing a substrate of a substantially solid material, the substrate having a first surface exhibiting a plurality of microelement protrusions being of at least one predetermined shape and size, each having a base-shape that forms a perimeter along the first surface, the substrate having a second substantially planar surface opposite the first surface, the substrate being substantially non-porous between the first and second surfaces; providing a mask plate having a third substantially planar surface and a fourth surface opposite the third surface, the mask plate exhibiting a plurality of openings formed between the third and fourth surfaces; placing the third substantially planar surface of the mask plate proximal to the second substantially planar surface of the substrate, and forcing a fluid under pressure from the fourth surface of the mask plate through the plurality of openings, thereby forming a plurality of fluidic jets under pressure; and forming a second plurality of openings in the substrate by way of the plurality of pressurized fluidic jets, wherein at least one of the plurality of microelement protrusions contain at least one of the second plurality of openings within their the perimeter.

In accordance with yet another aspect of the present invention, a method for constructing a microstructure is provided, in which the method comprises the following steps: providing a substrate of a predetermined solid material, the substrate having a first substantially planar surface and having a second substantially planar surface opposite the first surface, the substrate being substantially non-porous between the first and second surfaces; providing a first object having a first predetermined shape and a second object having a second predetermined shape, and positioning the substrate between the first object and the second object by placing the second substantially planar surface of the substrate proximal to the second object, while placing the first object proximal to the first substantially planar surface of the substrate; and simultaneously pressing the first object against the first surface and pressing the second object against the second surface of the substrate of solid material: (i) wherein the first surface is pressed by the first object, such that the first predetermined shape forms a plurality of microelement protrusions in the first surface, the plurality of microelement protrusions being of at least one predetermined shape and size, each having a base-shape that forms a perimeter along the first surface; (ii) wherein the second surface is pressed by the second object, such that the second predetermined shape forms a plurality of microholes within the substrate, at least one of the plurality of microholes extending completely through the substrate between the first and second surfaces; (iii) wherein at least one of the plurality of microelement protrusions contain at least one of the plurality of microholes within their the perimeter; and (iv) wherein the first predetermined shape of the first object and the second predetermined shape of the second object produce a self-aligning effect when the first and second objects are pressed toward one another in the pressing step.

In accordance with still another aspect of the present invention, a method for constructing a microstructure is provided, in which the method comprises the following steps: providing a substrate of a first material, the substrate having a first substantially planar surface and having a second substantially planar surface opposite the first surface, the substrate having a plurality of openings formed between the first and second surfaces; placing a second material into at least one of the plurality of openings, the second material having at least one property that is different from at least one property of the first material; pressing against the first surface of the substrate of material with an object having a predetermined shape to thereby form a plurality of microelement protrusions in the first surface, the plurality of microelement protrusions being of at least one predetermined shape and size, each having a base-shape that forms a perimeter along the first surface; and removing the second material from substantially all of the plurality of openings; wherein at least one of the plurality of microelement protrusions contain at least one of the plurality of openings within their the perimeter.

In accordance with a further aspect of the present invention, a method for constructing a microstructure is provided, in which the method comprises the following steps: providing a substrate of a first material, the substrate having a first substantially planar surface and a second substantially planar surface opposite the first surface, the substrate having a plurality of openings formed between the first and second surfaces; and pressing against the first surface of the substrate of material with an object having a predetermined shape to thereby form a plurality of microelement protrusions in the first surface, the plurality of microelement protrusions being of at least one predetermined shape and size, each having a base-shape that forms a perimeter along the first surface; wherein at least one of the plurality of openings are not completely closed by the pressing operation, and wherein at least one of the plurality of microelement protrusions exhibit at least one of the plurality of openings within their the perimeter.

In accordance with a yet further aspect of the present invention, a method for constructing a microstructure is provided, in which the method comprises the following steps: providing a substrate of a substantially solid material, the substrate having a first surface exhibiting a plurality of microelement protrusions being of at least one predetermined shape and size, each having a base-shape that forms a perimeter along the first surface, the substrate having a second substantially planar surface opposite the first surface, the substrate being substantially non-porous between the first and second surfaces; providing a mask plate having a third substantially planar surface and a fourth surface opposite the third surface, the mask plate exhibiting a plurality of openings formed between the third and fourth surfaces; placing the third substantially planar surface of the mask plate proximal to the second substantially planar surface of the substrate, and forcing a fluid under pressure from the fourth surface of the mask plate through the plurality of openings, thereby forming a plurality of fluidic jets under pressure; and forming a second plurality of openings in the substrate by way of the plurality of pressurized fluidic jets, wherein at least one of the plurality of microelement protrusions contain at least one of the second plurality of openings within their the perimeter.

In accordance with a still further aspect of the present invention, a method for constructing a microstructure is provided, in which the method comprises the following steps: providing a substrate of a substantially solid material, the substrate having a first surface exhibiting a plurality of microelement protrusions being of at least one predetermined shape and size, each having a base-shape that forms a perimeter along the first surface, the substrate having a second substantially planar surface opposite the first surface, the substrate being substantially non-porous between the first and second surfaces; providing a solid object having an upper surface with a predetermined shape, the shape comprising a plurality of projections which extend above a base member of the solid object; placing the upper surface of the solid object proximal to the second substantially planar surface of the substrate, and heating the solid object to a temperature that is greater than a melting point of the substrate material; and forming a plurality of openings in the substrate by allowing the plurality of projections to penetrate into the substrate due to melting of the substrate material at those locations, wherein at least one of the plurality of microelement protrusions contain at least one of the plurality of openings within their the perimeter.

In accordance with yet a further aspect of the present invention, a method for constructing a microstructure is provided, in which the method comprises the following steps: providing a substrate of a predetermined solid material, the substrate having a first substantially planar surface and having a second substantially planar surface opposite the first surface, the substrate being substantially non-porous between the first and second surfaces; providing a first object having a first predetermined shape and a second object having a second predetermined shape, and positioning the substrate between the first object and the second object by placing the second substantially planar surface of the substrate proximal to the second object, while placing the first object proximal to the first substantially planar surface of the substrate; and simultaneously pressing the first object against the first surface and pressing the second object against the second surface of the substrate of solid material: (i) wherein the first surface is pressed by the first object, such that the first predetermined shape forms a plurality of microelement protrusions in the first surface, the plurality of microelement protrusions being of at least one predetermined shape and size, each having a base-shape that forms a perimeter along the first surface; (ii) wherein the second surface is pressed by the second object, such that the second predetermined shape forms a plurality of microholes within the substrate, at least one of the plurality of microholes extending completely through the substrate between the first and second surfaces; (iii) wherein at least one of the plurality of microelement protrusions contain at least one of the plurality of microholes within their the perimeter; and (iv) wherein the first predetermined shape of the first object and the second predetermined shape of the second object produce a self-aligning effect when the first and second objects are pressed toward one another in the pressing step.

Still other advantages of the present invention will become apparent to those skilled in this art from the following description and drawings wherein there is described and shown a preferred embodiment of this invention in one of the best modes contemplated for carrying out the invention. As will be realized, the invention is capable of other different embodiments, and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated in and forming a part of the specification illustrate several aspects of the present invention, and together with the description and claims serve to explain the principles of the invention. In the drawings:

FIG. 3 is a top view, while the other views are elevational and section views.

FIG. 12 is a top view, while the other views are elevational and section views.

FIGS. 19 and 21 are top views, while FIGS. 20 and 22 are elevational, section views.

FIGS. 23 and 25 are top views, while FIGS. 24 and 26 are elevational, section views.

In FIG. 46, the bottom mold/die-half uses conical projections. FIGS. 46 and 47 are elevational views in cross-section, and FIG. 48 is a top plan view.

FIGS. 49 and 51 are elevational in partial cross-section views. FIG. 50 is a perspective view, and FIG. 52 is a top plan view. The bottom mold/half resembles a plus-sign in FIG. 50.

FIGS. 53 and 55 are elevational in partial cross-section views. FIG. 54 is a perspective view, and FIG. 56 is a top plan view.

DETAILED DESCRIPTION OF THE PREFERRED EMBODIMENT

Reference will now be made in detail to the present preferred embodiment of the invention, an example of which is illustrated in the accompanying drawings, wherein like numerals indicate the same elements throughout the views.

As described below, the present invention includes several different methodologies for manufacturing hollow microneedles, in which such microneedles can be of various lengths. The microneedles can be, for example, as long as 2000 microns or 3000 microns, or as short as, for example, a single micron. (A micron is a micrometer, which is $10^{-6}$ meters.) The shapes of the microneedles (or "microelements") can be made using various materials, even including metal if desired. In general, the methodologies discussed in this disclosure refer to polymer or plastic materials, or other low-cost formable materials, and in several of the structures disclosed below, there are two different materials used, both of which may be a polymer material or some other type of moldable or extrudable material.

Figure 1:
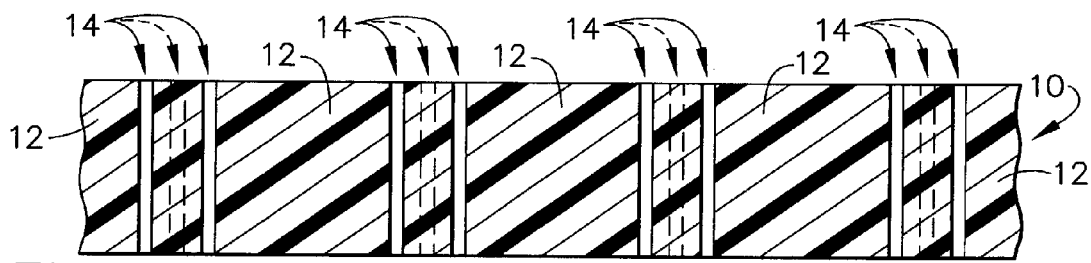
FIGS. 1-5 illustrate various steps in a process for creating an array of microelements on a microstructure, using a well-aligned system of holes and projections, as according to the principles of the present invention.

Referring now to FIG. 1, a first polymer or other type of extrudable or moldable material is formed as a sheet with multiple holes. The sheet is generally designated by the reference numeral 10, and the sheet itself consists of a substrate 12. The holes or openings formed within the sheet extend completely through the sheet, as illustrated at the reference numerals 14. The holes can be formed in a molding process, if desired, or perhaps a solid planar sheet of material is used to create the structure, after which the holes are formed in another manner, such as some type of stamping, or punch-press, or a drilling operation. In a high-production manufacturing methodology, it would probably be least expensive to provide the sheet with holes already pre-molded therein by the time the structure 10 of FIG. 1 is formed.

Figure 2:
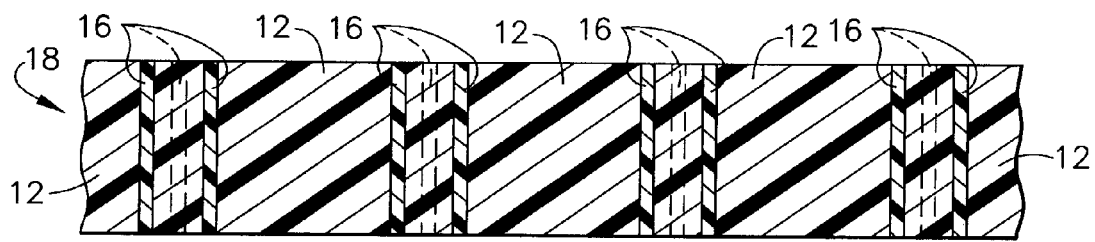

FIG. 2 shows the substrate material 12 that was illustrated in FIG. 1 as a first material, but the holes 14 have now been filled with a second type of material, preferably one that has a lower melting temperature than that of the first material. As can be seen in FIG. 2, what formerly were holes are now filled with plastic or other type of moldable material, generally designated by the reference numeral 16. The entire structure of FIG. 2 is generally designated by the reference numeral 18. So long as the melting point of the first material that makes up the substrate 12 is sufficiently high, the plastic "flowability" of the second material 16 can be made to be relatively low in viscosity, thereby making it fairly easy and quick to fill the openings 14, e.g., using a "bath" of the second material, then cooled to become the solid material 16.

Figure 3:
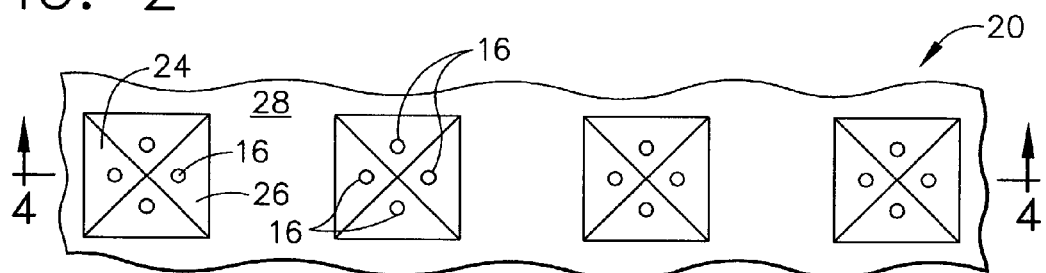
Figure 4:
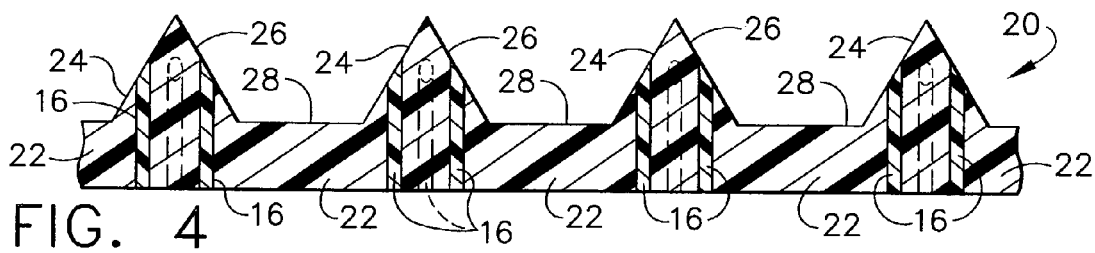

After the structure 18 has been accomplished as illustrated in FIG. 2, an embossing or other type of stamping, squeezing, or pressing action now takes place to form pyramidal microelements, as seen in FIGS. 3 and 4. As can be seen in FIG. 3, each microelement is shaped as a four-sided pyramid, in which the "left" face of the pyramid (as seen in FIG. 3) is designated at the reference numeral 24, while the "right" surface (as seen on FIG. 3) is designated at the reference numeral 26. Each microelement exhibits a base-shape (a square in the example of FIG. 3) that forms a perimeter along the top surface 28 of the substrate 22.

The filled columns of material 16 still remain within the microstructure 20 in FIGS. 3 and 4, although the entire structure with the pyramidal shape will create a situation in which the columns of the second material 16 no longer are of the same length as was seen in FIG. 2, and also their top surfaces are no longer perpendicular to the longitudinal axis of these cylindrical structures 16.

FIG. 4 shows the cross-sectional side view of these pyramidal structures taken along the line 4-4 of FIG. 3, and the left faces 24 and right faces 26 are easily seen for each of the microelements. The "top" planar surface between each pyramidal microelement is designated by the reference numeral 28 between each of the pyramid microelements. The substrate in FIG. 4 is now referred to by the reference numeral 22, because it no longer has two planar surfaces as was the case in the substrate 12 of FIG. 2. In the side cross-sectional view of FIG. 4, the top surface of each of the cylinders 16 has an elliptical shape, as one would expect when the top of the cylinder has been truncated along the angle that makes up the side faces of the pyramids. The overall microstructure in FIGS. 3 and 4 is referred to by the reference numeral 20, which now comprises an array of microelements (or "microneedles").

The embossing, squeezing, stamping, or pressing action that creates the shape illustrated in FIGS. 3 and 4 is meant to be a permanent deformation, which causes plastic deformation of the first material (of substrate 12) and also causes a plastic deformation of the second material that makes up the cylinders 16. In this first embodiment of the present invention, the second material of the cylinders 16 is not allowed to escape from the original holes 14, although if some of the material were to escape outside the surface, it may not cause a problem, especially along the "bottom" surface as seen in FIG. 4, since the material 16 will be ultimately removed (which will be discussed below in reference to FIG. 5).

Figure 5:
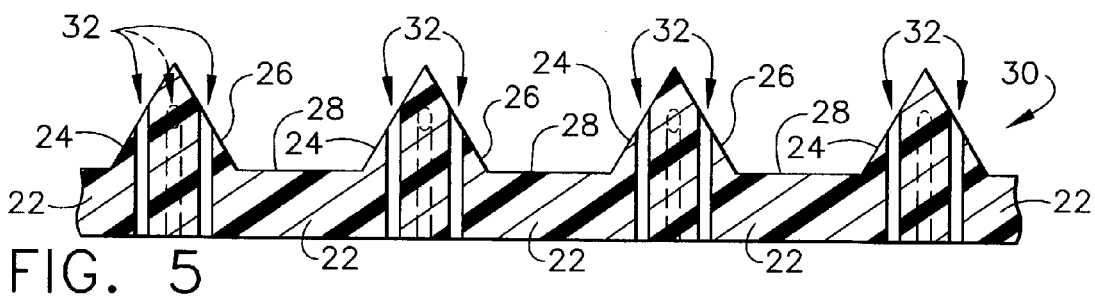

FIG. 5 illustrates the next step in the process, in which the second material that makes up the cylinders 16 is removed by raising the temperature of the structure above the melting point of this second material, but remaining below the melting point of the first material that makes up the substrate 22. The result in FIG. 5 is an array of hollow microelements, generally designated by the reference numeral 30. The "left" faces 24 and the "right" faces 26 still remain forming the pyramidal microelements, but the "old" cylinders of material 16 have now become openings 32 which extend completely through the structure 30.

As an alternative, the second material 16 of FIG. 4 can be removed by a chemical process that dissolves only this second material B, or perhaps which uses some other type of acidic or alkaline reaction involving a change in pH, or possibly some type of mechanical process which could literally drill or otherwise knock out the second material 16 from the locations that will become the openings 32. It will be understood that many types of methodologies could be used to remove the material 16 from the remaining substrate 22 of the structure 20 illustrated in FIG. 4, thereby achieving the structure 30 of FIG. 5. Some of the materials that could be used in the present invention include PMMA, which is a common abbreviation or acronym for the chemical polymethylmethacrylate. Another likely material that could be used in the present invention is PSF, which is an acronym for polysulfone. As an alternative, the material could be a dissolvable polymer that would enable some unique applications for the resulting microstructures.

In this first embodiment of FIGS. 1-5, the original holes or openings 14 are "well aligned" with the mold or die that will create the pyramidal microelements, thereby ensuring that the cylinders of the second material 16 are within the perimeter of the pyramids (microelements) that are to be formed between the steps of FIG. 2 to FIGS. 3 and 4. Therefore, the columns of material 16 remain within the "faces" of the pyramids as these pyramids are formed. There could be additional holes in the remaining planar substrate material (i.e., along the substrate areas at 28) if desired (either intentionally or "accidentally" due to a minor misregistration).

It will be understood that it is not critical for every hole 14 on FIG. 1 to be filled with the second material for this invention to be useful. The percentage of filled holes that later become openings 32 on FIG. 5 can be quite small, while nevertheless rendering a very functional structure.

Figure 6:
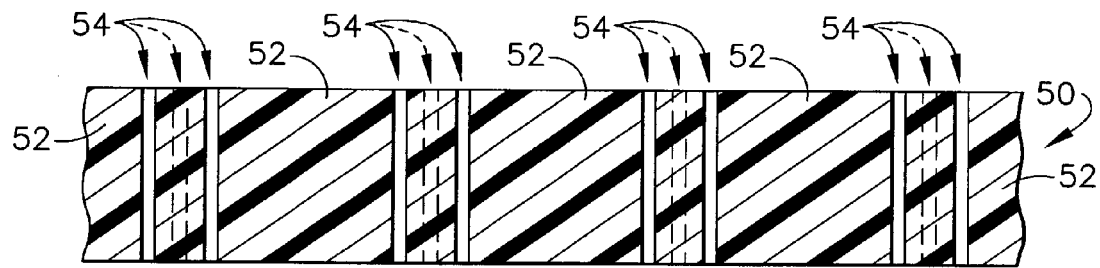
FIGS. 6-9 are elevational views in cross-section of another well-aligned system for creating an array of microelements on a microstructure, using a co-extrusion process, as according to the principles of the present invention.

Referring now to FIG. 6, another substrate with openings or through-holes is illustrated, generally designated by the reference numeral 50. The substrate material is indicated at 52, and the through-holes are indicated at 54. Again, this structure can be formed out of virtually any desired material, although if it is some type of plastic or polymer material, it could easily be molded with the holes already in place. Alternatively, the structure could be formed as a solid planar sheet of material, and the holes could be formed later by some type of drilling or punching process, if desired.

Figure 7:
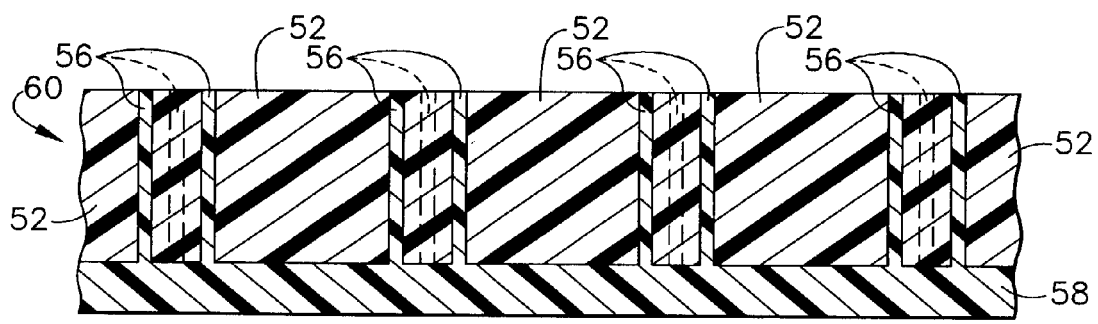

Once the structure 50 is formed, it may be fed through an extrusion machine and co-extruded with a second plastic or polymeric material to form the structure illustrated in FIG. 7. The second material would be co-extruded along the bottom (as seen on FIG. 7) of the structure 52, and this second material would be planar on its bottom surface and formed as a layer 58. The empty holes 54 of FIG. 6 would now become filled with the second material from the co-extruded layer 58, and these holes then become cylinders 56 of the second material, which could easily be accomplished if the second material has a lower melting or plastic deformation temperature. A more precise way of describing this is so that, during the co-extrusion step, the process temperature is raised to the transition temperature of the second material (of layer 58) so that this second material will exhibit plastic flow into the openings 54 of the first material that makes up the substrate layer 52. The resulting overall structure is designated by the reference numeral 60, and the substrate 52 has really not been affected at all, except to have its openings filled with the second material because of the plastic flow into those openings.

Figure 8:
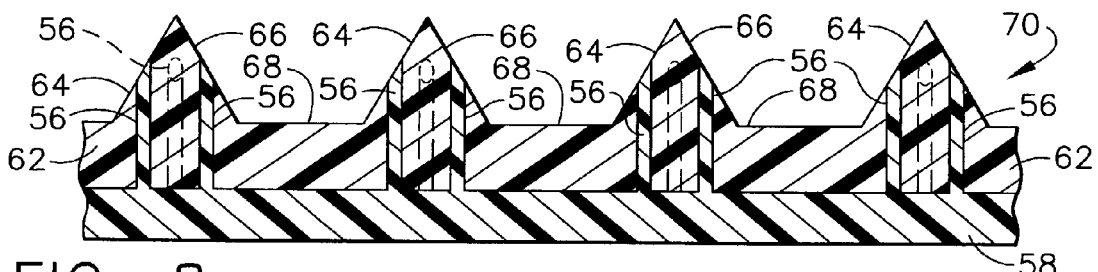

FIG. 7 provides the appearance of the two-layer co-extruded material, after which an embossing or other type of squeezing, stamping, or pressing action occurs to form the microstructure shapes illustrated in FIG. 8. In this design, FIG. 8 looks much like FIG. 4, described above, except that FIG. 8 also has a second layer of (the second) material at 58. The structure 62 on FIG. 8 is virtually identical to the structure 22 of FIG. 4, which exhibits four-sided pyramids as individual microelements, each having a "left" face (as seen on FIG. 8) 64, a "right" face (as seen on FIG. 8) 66, and with an open planar top surface 68 between each of the microelements. The cylinders 56 of the second material have now been truncated by the die or mold that is used during the embossing/squeezing/pressing step, and therefore, has the appearance as seen on FIG. 8. From a top view, the structure 70 of FIG. 8 would look much like that of FIG. 3 for the structure 20.

Figure 9:
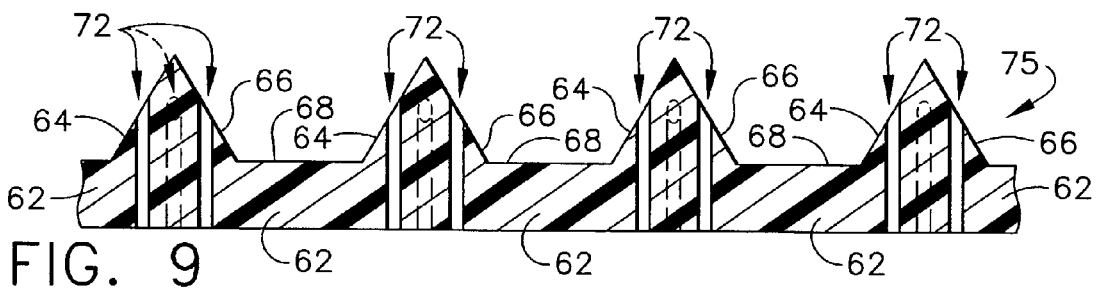

To obtain the "final" microstructure 75 that is illustrated in FIG. 9, the second material must be removed. This can be done by raising the temperature above the plastic melting point of the second material 58 (but remaining below the melting point of the first material that makes up the substrate 62), or perhaps it could be done by use of some type of acidic or alkaline reaction that involves a change of pH, or some other type of chemical reaction, or possibly even some type of mechanical operation. The end result is a structure 75 in FIG. 9 which exhibits open through-holes 72 that extend from the bottom of the substrate 62 through the faces 64 and 66 of the pyramidal microelements. As part of the chemical or thermal process to move from the structure 70 of FIG. 8 to the structure 75 of FIG. 9, the bottom layer 58 of the second material will also be removed from the substrate material 62 made of the first material.

In a similar fashion to the structures described in reference to FIGS. 1-5, the structures illustrated in FIGS. 6-9 are formed by another "well-aligned" system by which the original through-holes are aligned with the die or mold that creates the pyramidal microelements, such that the "filled holes" 56 are within the perimeter and become part of the faces of the individual pyramids that make up the microelements. If desired, holes through the planar top portions 68 of the substrate may also be included in this microstructure.

Figure 10:
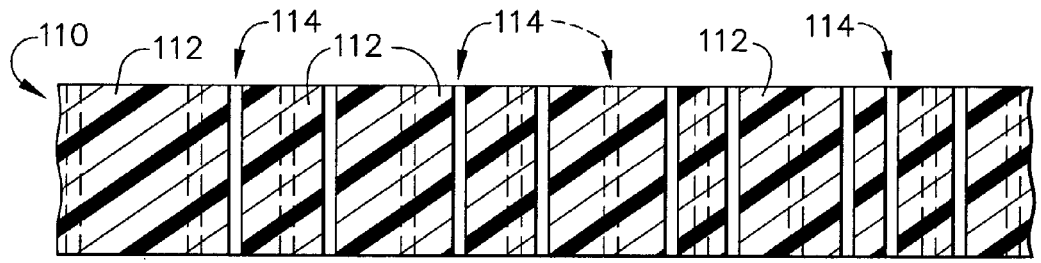
FIGS. 10-14 illustrate various steps in a process for forming an array of microelements on a microstructure, in which the openings are located in a semi-random manner with respect to the projections that are formed as the microelements, as according to the principles of the present invention.

FIG. 10 is another cross-sectional view of a substrate material that has holes formed therethrough, in which the structure is generally designated by the reference numeral 110. The substrate material itself is indicated at 112 and the through-holes or openings are designated at 114. The material used for this structure 110 could be of virtually any type of solid desired by a designer, and would likely be some type of moldable or extrudable polymer or plastic material that could have the holes molded at the same time the planar substrate is manufactured; or the substrate could be manufactured as a solid planar sheet and the openings or through-holes could be formed later by any number of ways.

Figure 11:
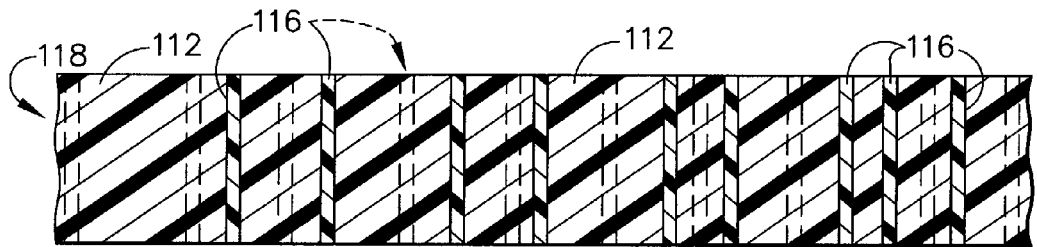

FIG. 11 shows the same substrate 112 after a second material has been added to the structure (using a heated bath of the second material, for example), which is now generally designated by the reference numeral 118. The former holes or openings 114 have now become filled with the second material, and these cylindrical shapes are designated by the reference numeral 116. The structures of FIG. 10 and FIG. 11 are quite similar to those described above in reference to FIGS. 1 and 2. In general, the material 116 would be selected to have a lower melting temperature than the first material 112, and therefore, the material 116 could easily flow into the openings 114 when making the transition from the structure 110 of FIG. 10 to the structure 118 of FIG. 11.

Figure 12:
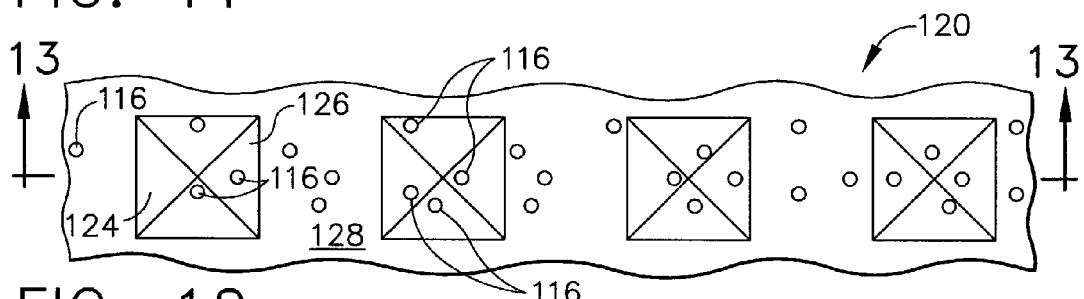
Figure 13:
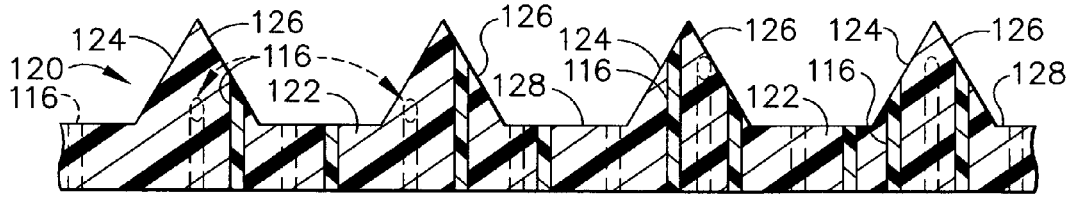
Figure 14:
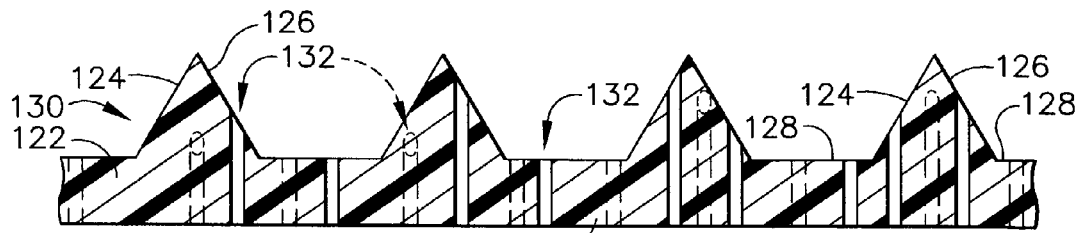

As will be seen by inspecting the views of FIGS. 12-14, the holes 114 which become cylinders of the second material 116 are not "well-aligned" and instead are formed in positions that are semi-random. The result of this is that many of the cylinders of the second material 116 will not end up at locations that are within the perimeter and which would become part of the projections that have been referred to above as pyramidal microelements. Therefore, many of the cylinders 116 of the second material will be formed in the relatively planar areas 128 between the individual microelements, and thus many of the openings formed in the final process step that leads to the structure of FIG. 14 will be in locations that do not necessarily assist in dispensing a liquid through a skin barrier or membrane barrier. On the other hand, the semi-random holes will have a sufficiently high density and thus be spaced with sufficiently small distances therebetween that a large number of them will still end up within the microelement perimeter positions, and therefore, such openings will assist in dispensing liquid through such skin barriers or membrane barriers.

Referring now to FIG. 12, the individual four-sided pyramids will have perimeters that encompass many of the cylinders 116 of the second material, which is easily discerned from this top view. The individual microelements still contain a "left" face (as seen in FIG. 12) at 124, and a "right" face (as seen in FIG. 12) at 126. The planar surface between each of the individual pyramidal microelements is designated by the reference numeral 128, and the entire microelement array (or microstructure) is generally designated by the reference numeral 120.

FIG. 13 is a cross-sectional view from the side of the top view of FIG. 12, taken along the line 13-13. In FIG. 13, the left faces 124 and right faces 126 of the individual pyramidal microelements are easily seen, and the overall structure that was once a planar substrate is now designated by the reference numeral 120. Each of the cylinders of material are easily seen at 116 in FIG. 13, and many of these cylinders penetrate through one of the faces of a pyramidal microelement, while others of these cylinders 116 of the second material only penetrate to one of the planar surfaces 128.

The structure of FIGS. 12 and 13 is once again formed by an embossing procedure, or some type of pressing action and, as noted above, the individual microelements will not be "well-aligned" with any group of the original holes 114 that become the cylinders of the second material 116. (It will be understood that the words "press" or "pressing" herein can refer to any type of punching, stamping, or squeezing procedure, including "embossing," and thus, all of these alternative words will not be used every time herein when describing such functions.) As also noted above, the number and density of these holes 114/cylinders 116 will be sufficiently high such that a large number of the pyramidal microelements will have at least one through-hole when the structure is finished (as seen at FIG. 14).

The final step in creating the structure 130 of FIG. 14 is to remove the second material that remains in the cylindrical columns 116 of the structure 120 illustrated in FIG. 13. This can be done chemically, or by raising the temperature such that it exceeds the melting point of the second material (which makes up the cylinders 116) but nevertheless remains below the melting temperature of the first material that makes up the substrate structure 122. In either instance, the cylindrical material 116 is removed, thereby leaving the structure 130 illustrated in FIG. 14. There are now a large number of openings or through-holes 132, many of which extend through one of the faces of the pyramidal microelements, and others of which extend from the bottom surface of the substrate 122 through to the top planar surface at 128. Of course, the openings 132 that penetrate through to one of the faces of a pyramidal microelement will more likely assist in delivering a liquid from the bottom surface through the top surface and through a layer of a skin structure or a membrane structure.

It will be understood that the present invention is not constrained by a particular size or shape of the individual microelements, and this includes the height of the microelements and the spacing between such individual microelements. Of course, the well-aligned embodiments will have some predetermined distance between each set of microelements, but that distance can be virtually any dimension that is desired by the structure designer. In some embodiments, it might be best if the thickness of the plastic film that can make up the original substrate layer (e.g., substrate 12 of FIG. 1) should be selected to ensure some flexibility, thereby enabling the substrate structure to somewhat conform to irregular shapes. Again, this can be up to the structure designer. As to physical dimensions, in reference to FIG. 5, the distance between the top and bottom surfaces of the substrate 22 could, for example, be in the range of about 100 microns, while the distance between the base and tip of each of the pyramidal microelements could, for example, be about 160 microns. It cannot be emphasized enough that the actual shapes and dimensions of the microelements are up to the system designer, and virtually any size or shape is contemplated by the inventors of the present invention. Some example shapes that could be used are illustrated in FIGS. 34-45. Yet further shapes of pyramidal microelements are further illustrated in FIGS. 46-56, which will be described below in greater detail.

Figure 15:
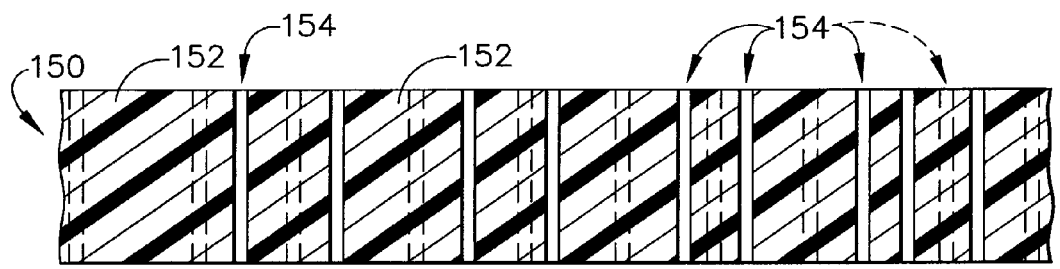
FIGS. 15-18 are elevational views in cross-section of various steps used to create an array of microelements on a microstructure in which the holes are located in a semi-random fashion, using a co-extrusion process, as according to the principles of the present invention.
Figure 16:
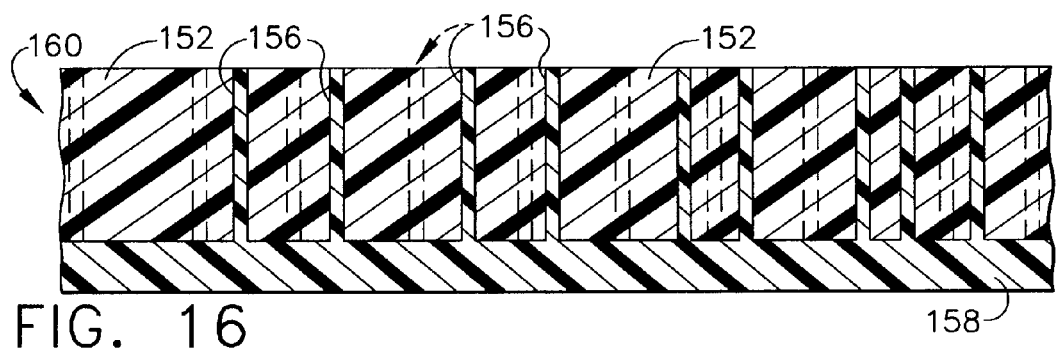

Referring now to FIG. 15, a starting structure generally designated by the reference numeral 150 includes a substrate 152 with multiple through-holes or openings 154. As was the case in FIG. 10, this structure can be made of virtually any material desired by the structure designer, although such material preferably is either moldable or extrudable. The holes 154 can be molded directly upon manufacturing of the substrate 152, or the substrate 152 can start as a smooth planar sheet, after which the holes are added by some type of mechanical or chemical operation, or even an optical operation (e.g., a laser burn to create the holes).

The next step in the process is to perform a co-extrusion procedure, by which an added layer of a second material at 158 is formed along the bottom surface of the substrate 152, thereby creating an overall structure generally designated by the reference numeral 160. The previous openings 154 have now become filled with the second material and become columns or cylinders 156. So far this procedure is virtually identical to that described above in reference to FIGS. 6 and 7.

Figure 17:
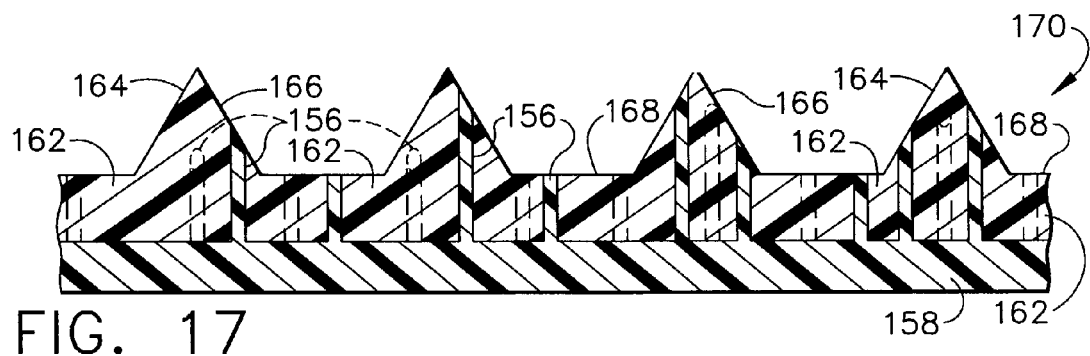

The next step is to emboss or otherwise press (or squeeze or stamp) a die or mold against the top surface of the structure 160, thereby forming multiple pyramidal microelements as seen in FIG. 17. This overall structure is generally designated by the reference numeral 170, and forms multiple four-sided microelements with "left" faces 164 (as seen in FIG. 17) and "right" faces 166 (as seen in FIG. 17), while also forming a relatively flat planar substrate top surface at 168. Many of the cylinders of the second material 156 have been truncated back to the smallest possible size at the planar surface 168, while others penetrate all the way to the top of one of the pyramidal faces at 164 or 166. As described above in reference to FIGS. 10-14, the holes 154/cylinders 156 are not "well-aligned" in the embodiment described in FIGS. 15-18, and thus many of the cylinders 156 do not line up within the perimeter of one of the pyramidal microelements. However, the number and density of these cylinders 156 are sufficient to ensure that most if not all of the microelements have at least one such pyramid or column 172 of the second material, which will become an opening by the time the structure is finished.

Figure 18:
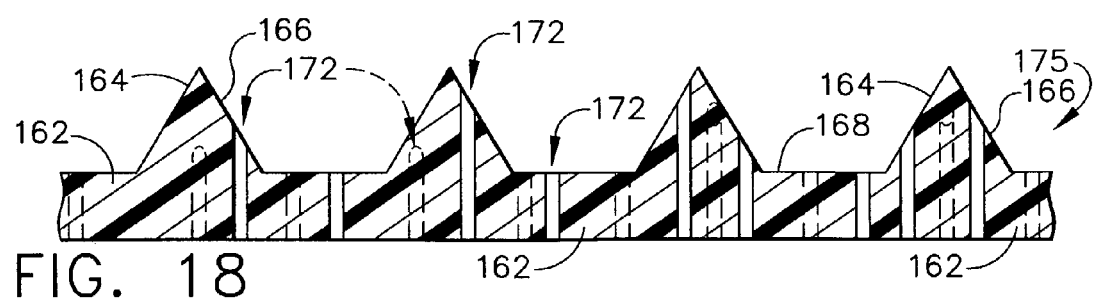

FIG. 18 shows the final structure, in which the second material has been removed, including the bottom layer 158. This removal procedure is done by raising the temperature to above the melting point of the second material, or perhaps by a chemical or other type of acidic or alkaline operation. What were cylinders 156 now become openings 172, and the overall structure is generally designated by the reference numeral 175. The structure of FIG. 18 is virtually identical to the structure of FIG. 14, and the only difference is that the manufacturing steps were somewhat different because of the co-extrusion process that formed the structure 160 of FIG. 16. In such a co-extrusion process, it is very likely that both materials (i.e., the materials that make up the substrate 152 and the bottom layer 158) will be some type of plastic or polymeric material, such as PMMA (of two different chains).

Figure 19:
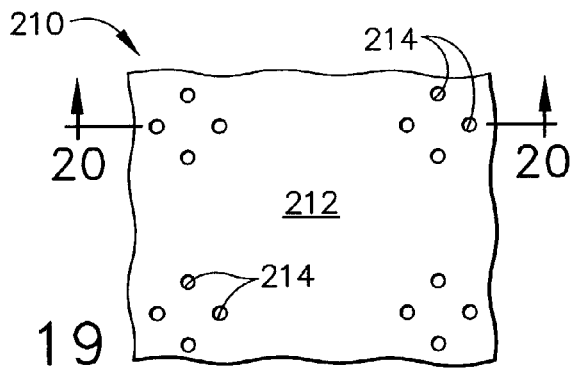
FIGS. 19-22 illustrate the steps in the construction of an array of microelements on a microstructure, in which the openings are well-aligned with respect to the individual microelements that are formed, and in which there is only a single material involved in the process, as according to the principles of the present invention.
Figure 20:
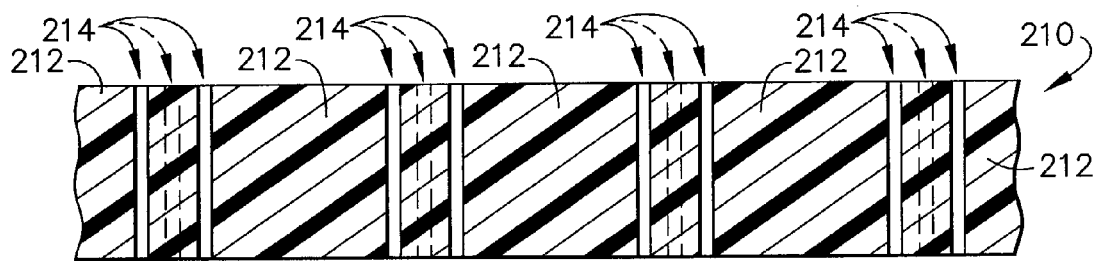

Referring now to FIG. 19, a sheet of material, such as a porous polymer sheet, is illustrated that has a large number of holes or openings. The overall structure is generally designated by the reference numeral 210, while the sheet material itself is designated at 212, and the holes at 214. FIG. 20 is a cross-section view taken along the line 20-20 of FIG. 19, and shows that the openings 214 are through-holes that extend all the way through the sheet or substrate 212. In this embodiment, a second material is not used to fill the holes 214, and the sheet 210 will be embossed (or pressed) directly as it exists in FIG. 20.

Figure 21:
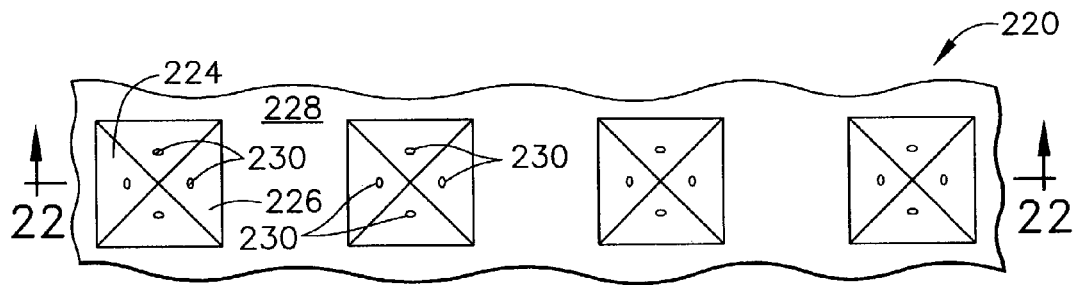
Figure 22:
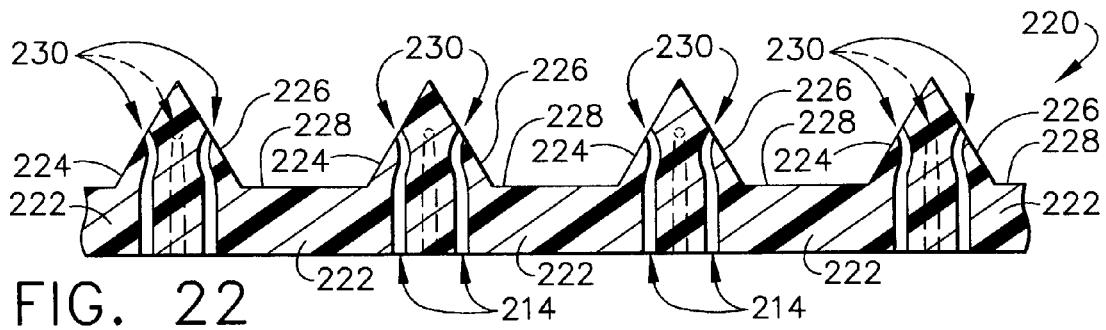

In FIG. 21, the embossing (pressing) step has already taken place, and a series of four-sided pyramids have been formed on the top surface of the sheet, as also seen in FIG. 22. In FIG. 21, the overall structure is generally designated by the reference numeral 220, and each of the pyramids has a "left" face (as seen in these views) at 224, a "right" face (as seen in these views) at 226, and a plurality of through-holes 230. The top planar surface of the substrate material is designated at 228.

FIG. 22 is a cross-section view, taken along the line 22-22 of FIG. 21, and it can be seen that the through-holes are somewhat deformed by the embossing step. The upper portions of these holes are designated by the reference numeral 230, and are not perfectly straight or uniform in diameter, mainly due to the partial crushing of the material about the openings. The bottom portions of the openings are still designated 214, because they have been unaffected by the embossing step. However, the top openings have been somewhat deformed.

As can be seen from the views FIG. 19-22, the holes are "well-aligned" with respect to the perimeter positions of the pyramidal microelements that become formed in the original planar sheet 210. This ensures that a number of openings will extend all the way through the protruding microstructures themselves, which will aid in the dispensing of a fluid from one side of the final structure 220 to the other side, while also penetrating through at least one layer of a skin barrier or a membrane.

With the proper selection of materials and embossing or pressing operations, the process can be such that the holes will not be entirely closed during the formation step of the microelements from the original planar sheet material 210. The use of more than one such opening per microelement can help ensure that at least one open hole will remain after the embossing step has taken place. As seen in FIGS. 21 and 22, with a well-aligned set of openings, there can be an individual hole 230 per face of the four-sided pyramids that make up the microelements themselves. Of course, other shapes for the microelements can be utilized, and more than one hole can be placed within a particular face of a microelement surface, if desired. It will be understood that other materials can be used for this type of structure, although care must be taken to use a material along with an embossing or pressing operation that will tend to not deform the holes so that they would become totally closed by the time the microelements have been formed in the sheet's top surface.

It will be understood that it is not critical for every hole 214 on FIG. 20 to remain opening after the embossing/pressing step occurs, for this invention to be useful. The percentage of holes 214 that later become openings 230 on FIG. 22 can be quite small, while nevertheless rendering a very functional structure.

Figure 23:
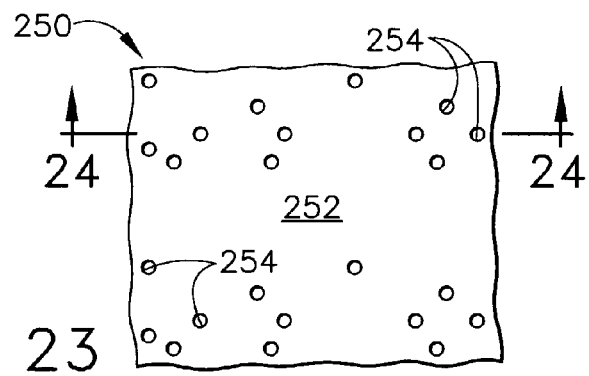
FIGS. 23-26 show the steps in constructing an array of microelements on a microstructure in which the openings are located in a semi-random manner as compared to the locations of the individual microelements, and in which there is only a single material involved in the process, as constructed according to the principles of the present invention.
Figure 24:
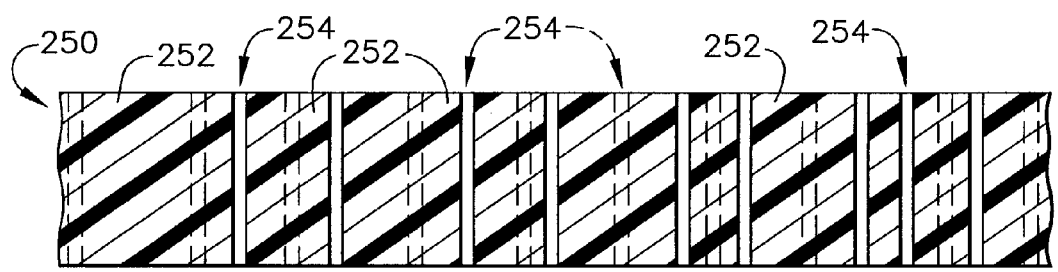

Referring now to FIG. 23, another sheet of material is utilized with multiple openings or holes, in which the overall structure is generally designated by the reference numeral 250. The sheet material itself is designated by the numeral 252, and the openings are designated at 254. FIG. 24 is a cross-section view from the side of this structure, taken along the line 24-24 of FIG. 23. As can be seen in FIG. 24, the holes or openings 252 extend completely through the planar sheet structure 252.

The sheet structure 250 is essentially the same as was described in FIG. 19 of the sheet structure 210. The main difference is that the locations of the holes 254 are semi-random, rather than being well-aligned. Therefore, after an embossing or pressing step is performed on the sheet structure 250, some of the holes 254 will not be located within the perimeter of a microelement that protrudes from the top surface of the sheet. This can be seen in FIGS. 25 and 26, which illustrate the microstructure 260 after the embossing step has been performed, and a series of four-sided pyramids now protrude from the top surface 268 of the structure, generally designated by the reference numeral 260.

Figure 25:
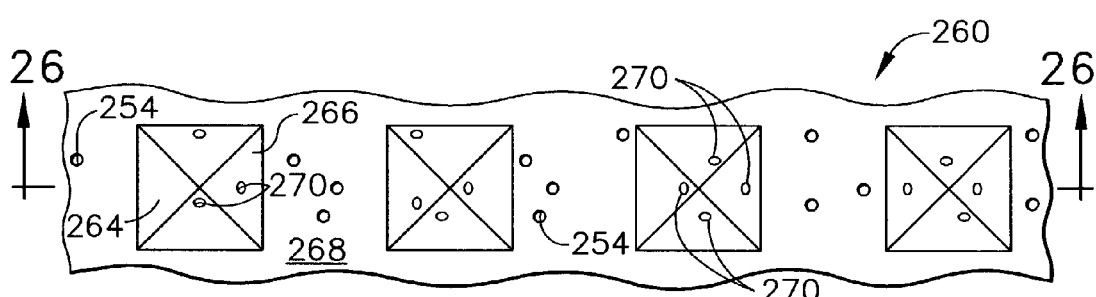

In FIG. 25, each four-sided pyramid has at least one opening 270, and these pyramids each have a "left" face 264 and a "right" face 266 (as seen in these views). The top surface of the planar structure between each of the microelements is designated at 268.

Figure 26:
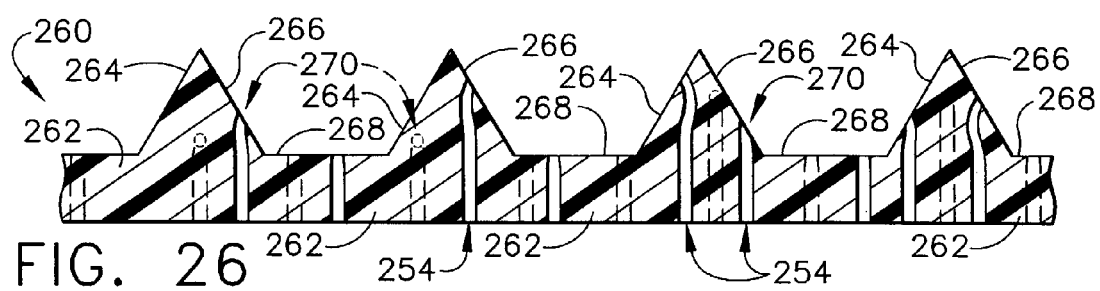

As can be best seen in FIG. 26, the upper portions of the openings have become somewhat deformed, but are not completely closed by the embossing or pressing step. The bottom portions of the holes are still designated 254 because they have not been affected by the embossing step, while the top portion of the holes are now designated 270, and have been somewhat deformed in both their longitudinal direction and in a non-uniform diameter. Some of the holes are not located within one of the pyramidal microelements, and protrude from the bottom surface of the substrate 262 to its top surface at 268. These openings will not likely be as useful in dispensing a liquid through a skin layer or membrane layer, as compared to the through-holes that extend into a microelement at 270.

Figure 27:
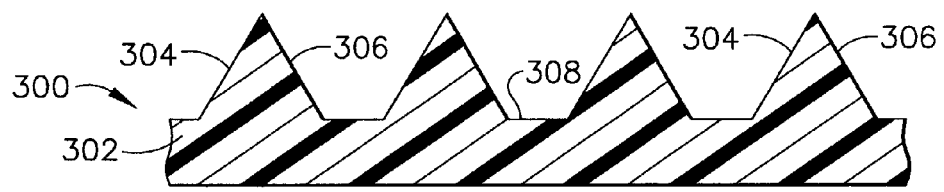
FIGS. 27-29 show the steps in a process of forming an array of microelements on a microstructure, in which through-holes are manufactured by use of a mask plate and either gas or liquid jets under pressure, as constructed according to the principles of the present invention. Each of these views is an elevational view in cross-section.

Referring now to FIG. 27, a microstructure generally designated by the reference numeral 300 is provided having a substrate 302 and a series of pyramidal microelements, each having a "left" face 300 (as seen on FIG. 27) and a "right" face 306 (as seen on FIG. 27), and each of these microelements has a planar spacing therebetween, designated at 308. The microstructure 300 of FIG. 27 can be made of virtually any material, however, as will be described below, a plastic or resin material would probably be preferred for the purposes of creating openings through the microstructure from its bottom surface to its top surface, either at the planar surfaces 308, or through one of the microelements themselves.

To form through-holes, a high pressure liquid or a hot gas stream (e.g., a fluid stream) is used to mechanically force openings through the solid, non-porous material of the microstructure 300. As an alternative, a gas or liquid (fluidic) stream that tends to chemically dissolve the material of the microstructure 300 could be used. A mask plate 310 (see FIG. 28) is brought against the bottom planar surface of the microstructure 300, and this mask plate has a large number of openings or through-holes at 312. The mask plate 310 can be made from metal, ceramic, or even silicon, if desired. If made of metal, the holes 312 could be made by stamping or drilled, or the plate with holes could be made from a casting procedure. A silicon plate 310 could be made from semiconductor fabrication techniques, for example.

Figure 28:
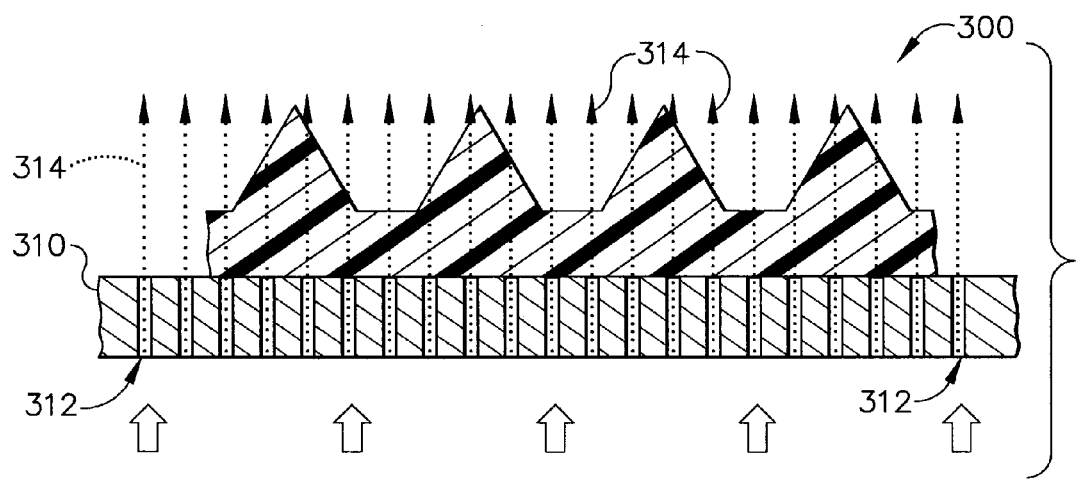

A gas or liquid (i.e., a fluid) is exerted under pressure along the bottom side (as seen in FIG. 28) of the mask plate 310, which tends to direct the gas or liquid upward and against certain locations of the microstructure 300. After a predetermined time of exposure to the high pressure liquid or gas (fluid), openings will be formed in the material of the microstructure 300, at the locations represented by the dotted arrows 314 on FIG. 28. These openings will be formed at a rate depending upon the temperature and pressure of the liquid or gas, or upon the chemical reaction rate of a gas or liquid (fluid) stream that tends to chemically dissolve the material of the microstructure 300.

Figure 29:
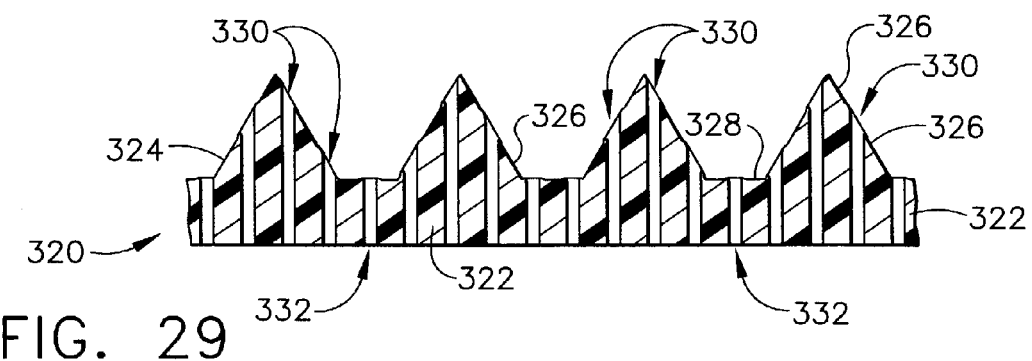

Once the microstructure 300 has been exposed to the high pressure gas or liquid (fluid) for a sufficient time period, the openings will be formed and the mask plate 310 can be removed, thereby leaving behind a microstructure with multiple protruding microelements and multiple through-holes, generally designated by the reference numeral 320 (see FIG. 29). Each of the pyramidal microelements still has a "left" face at 324 and a "right" face at 326 (as seen on FIG. 29). Moreover, each microelement preferably has at least one through-hole at 330, and there are also further through-holes at 332 in the overall structure 320 that protrude from the bottom surface to the planar top surface at 328 between the individual microelements.

During the manufacturing step of FIG. 28, it would probably be preferred for the microstructure to be held in place against the mask plate 310 by air or liquid (fluidic) pressure. If this "pressure methodology" is used to hold the microstructure 300 in place against the plate 310, then the bottom "jet" pressure must be greater than the top "holding" pressure, thereby enabling the gas or liquid (fluid) stream to protrude through the top surface of the microstructure to form its final shape at 320 on FIG. 29. Of course, any shape of microelement could be used in this method of manufacturing, as desired by the structure designer, and moreover, many different materials could be utilized, including PMMA.

Figure 30:
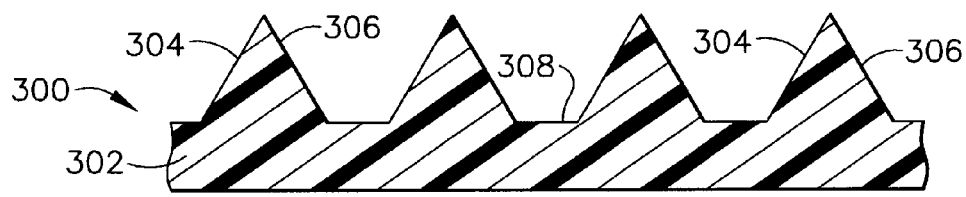
FIGS. 30-33 show the steps in a process for forming an array of microelements on a microstructure which uses a heated bottom mold to form openings in the microstructure, as constructed according to the principles of the present invention. Each of these figures is an elevational view in cross-section.

Referring now to FIG. 30, a microstructure generally designated by the reference numeral 300 is again provided that has a substrate 302 and a large number of individual microelements, in this case shaped like four-sided pyramids. Each of the microelements in this example structure 300 has a "left" face 304 and a "right" face 306 (as seen in FIG. 30), and there is a planar upper surface 308 between each of the individual microelements. In this embodiment, the entire structure 300 is made of a single material and as a unitary one-piece construction. It can be manufactured by many various techniques, several of which have been disclosed in patent documents by the same inventors, as noted above.

Figure 31:
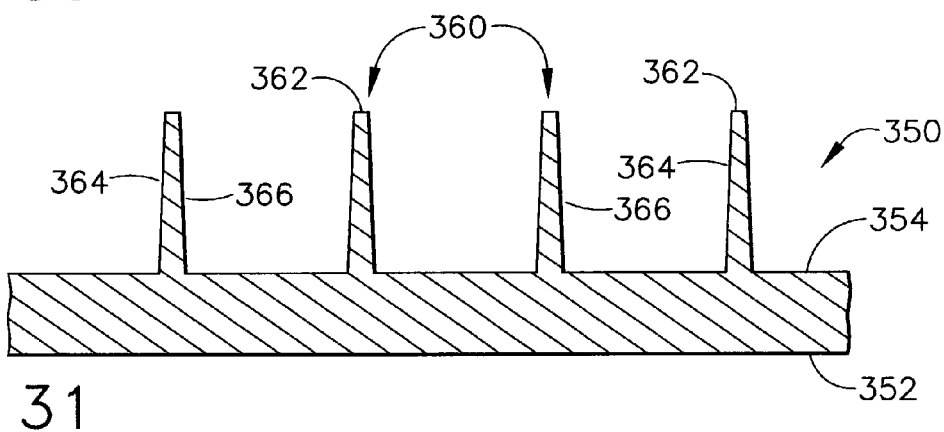

FIG. 31 illustrates a cross-section of a mold-structure, sometimes referred to as tooling, generally designated by the reference numeral 350, that will be used in conjunction with the microstructure 300 of FIG. 30. The mold structure 350 includes a base structure having a bottom planar surface 352 and a top mainly planar surface 354. There are multiple projections 360 that extend or protrude from the top surface 352. Each projection 360 has a "left" raised wall surface 364 and a "right" raised wall surface 366 (as seen in FIG. 31) as well as a top surface 362. This mold structure 350 could be made of many different materials, including metal, silicon, or a ceramic material. The mold structure is typically heated and then pushed against the bottom surface of the microstructure 300.

Figure 32:
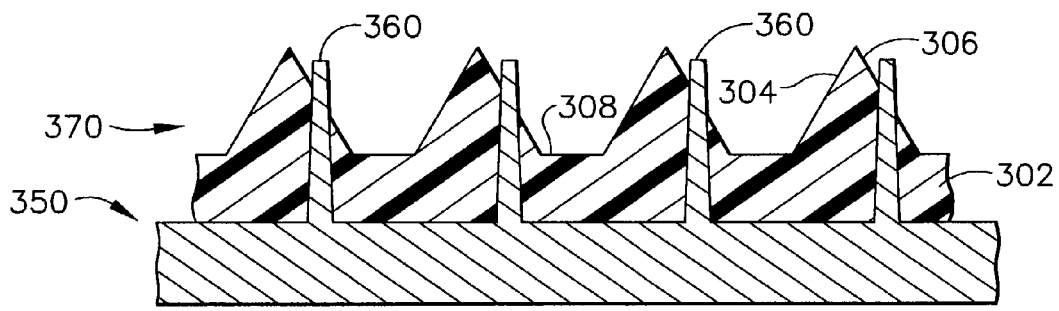
Figure 33:
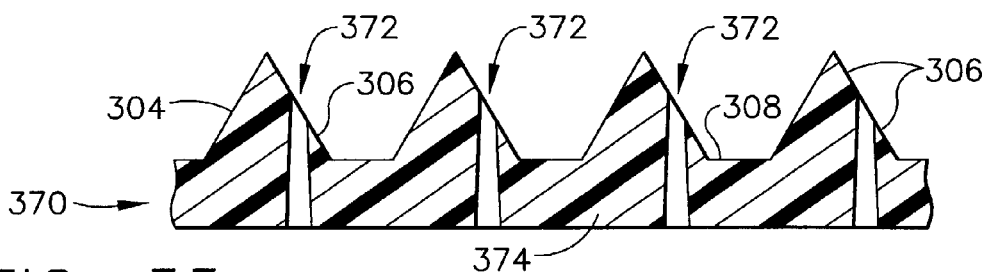

FIG. 32 shows the result of the heated mold structure 350 being pushed against the bottom surface of the microstructure 300. In this circumstance, the protrusions 360 have penetrated all the way through the microstructure, now designated 370, and have formed channels within the microstructure that protrude through the individual pyramidal-shaped protrusions, as seen in the view. The microstructure 370 mainly retains its original shape, and still has its "left" face 304 and "right" face 306 for each of the microelements, as well as retaining its mainly planar flat surface 308. Once the mold structure 350 has been cooled and is removed, the final microstructure 370 is the result, as illustrated in FIG. 33. Each of the microelements now has an opening or through-hole 372 in its "right" face 306.

It will be understood that multiple penetrations can be made in each of the microstructures, if desired by the microstructure designer, and also it will be understood that the structure sizes and shapes, as well as the angles of the sloped faces can vary without departing from the principles of the present invention. The angle between the top face 354 and one of the raised side-walls 364 or 366 should probably be a minimum of 90°, and preferably will be somewhat greater than 90° so that the protrusions 360 will more easily initially penetrate into the microstructure 300, and then later more easily release from the microstructure 300 after the penetrations have been made.

Figure 34:
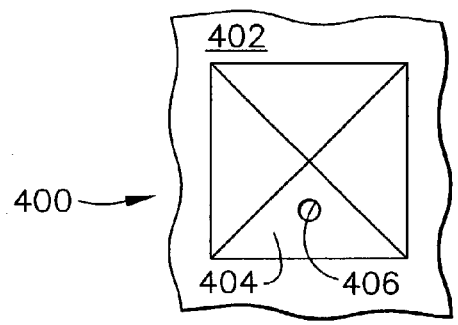
FIGS. 34 and 35 show a four-sided pyramid as a microelement, as a top view and a perspective view, respectively.
Figure 35:
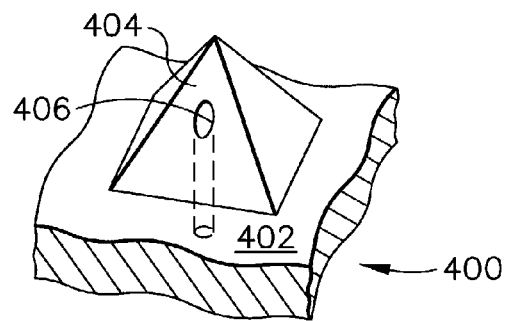

Several examples of some of the various shapes for individual microelements are provided in FIGS. 34-45. In FIGS. 34-35, the four-sided pyramid is illustrated as part of a microstructure 400. The top planar surface of the substrate is indicated at 402, while one of the faces of the pyramid is indicated at 404, which has a through-hole or opening at 406.

Figure 36:
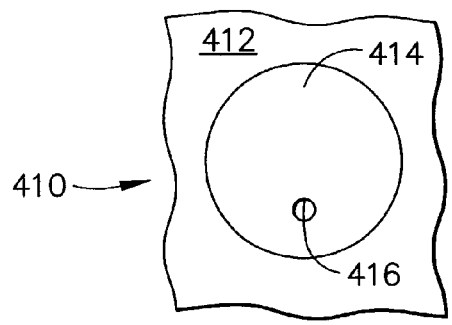
FIGS. 36 and 37 show a conical microelement, as a top view and perspective view, respectively.
Figure 37:
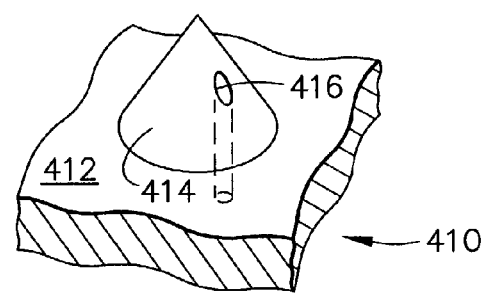

A cone-shaped microelement is illustrated in FIGS. 36-37 as part of a microstructure 410. The planar top surface of the substrate is indicated at 412, and the conical microelement protrudes upward and has a side wall structure at 414, and a through-hole or opening 416.

Figure 38:
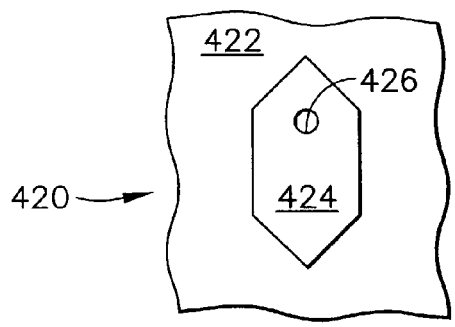
FIGS. 38 and 39 show a horizontally-oriented double-wedge-shaped microelement structure, as a top view and a perspective view, respectively.
Figure 39:
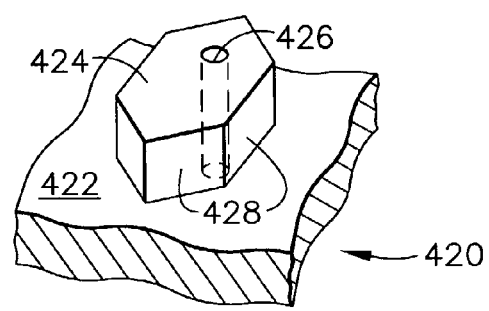

A wedge-shaped microelement is illustrated in FIGS. 38-39 as part of a microstructure 420, in which the microelement has two wedge edges. The top planar surface of the substrate is indicated at 422, and the individual microelement has a top planar surface at 424. The microelement has mainly vertical side walls at 428, and the top surface 424 exhibits a through-hole or opening 426.

Figure 40:
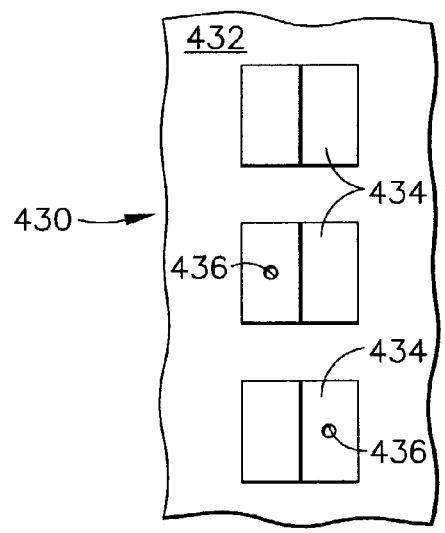
FIGS. 40 and 41 show a set of vertically-oriented wedge structures as a microelement, in a top view and a perspective view, respectively.
Figure 41:
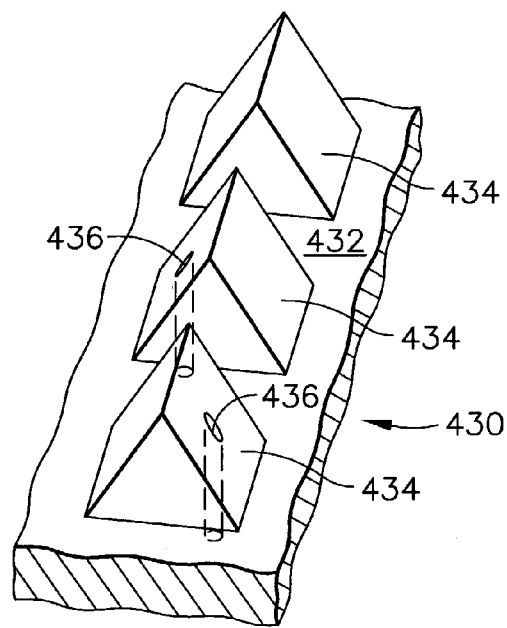

FIGS. 40 and 41 illustrate a microstructure 430 that is made up of multiple wedge-shaped microelements that are spaced-apart from one another on top of a substrate surface 432. Each of the wedge-shaped microelements has upward angled side walls 434, and some of the side walls 434 exhibit a through-hole or opening 436. A larger structure can have these microelements 434 spaced around on top of the substrate 432 in groups of three, as illustrated in FIGS. 40-41.

Figure 42:
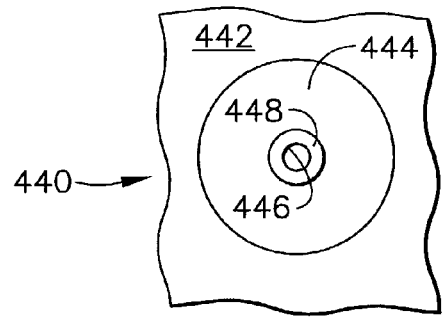
FIGS. 42 and 43 show a truncated conical microelement, in a top view and a perspective view, respectively.
Figure 43:
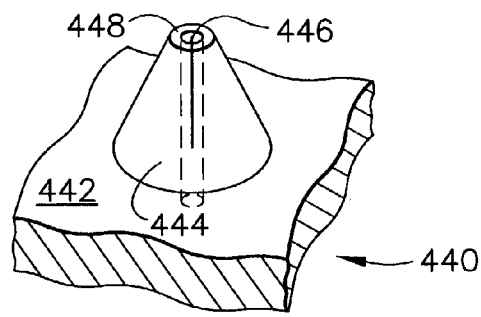

FIGS. 42 and 43 illustrate a microstructure 440 that has a truncated conical microelement. The top planar surface of the substrate is indicated at 442, and the conical upward, angled surface of the microelement is indicated at 444. The truncated top surface of the microelement is indicated at 448, which exhibits a through-hole or opening 446.

Figure 44:
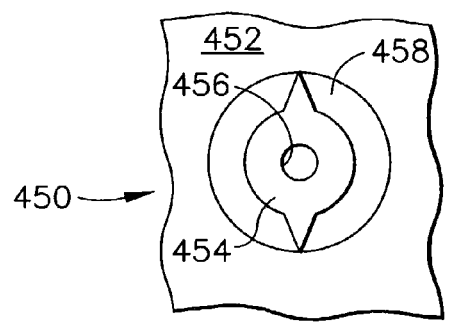
FIGS. 44 and 45 show a sharp-edged hollow microneedle, in a top view and a perspective view, respectively.
Figure 45:
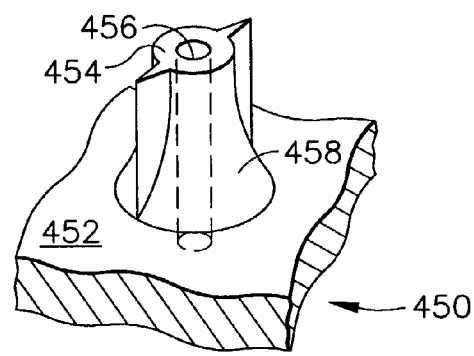

A hollow microneedle structure with "sharp" edges is illustrated in FIGS. 44 and 45 as part of a microstructure 450. The microneedle protrudes from the upper planar surface 452 of the substrate, and projects upward along a side wall 458. The uppermost surface of the microelement or microneedle is indicated at 454, which exhibits a through-hole or opening 456.

It will be understood that the various shapes of microelements illustrated in FIGS. 34-45 are only a sampling of the possible sizes and shapes that can be used to form microstructures, according to the principles of the present invention. Many other shapes have been disclosed by the same inventors in various patent documents, as noted in the above listing of patent documents incorporated by reference.

Figure 46:
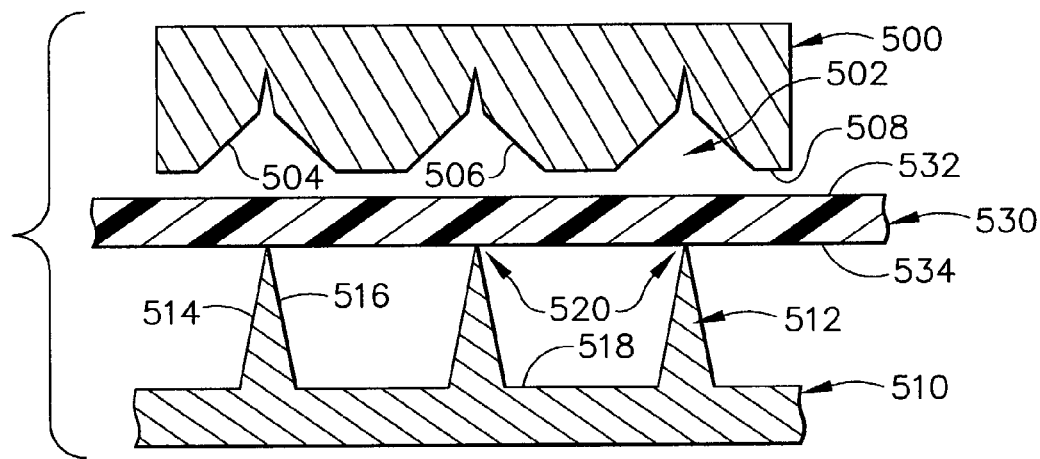
FIGS. 46-48 show the process steps in forming a set of well-aligned microelements on a microstructure, using two mold/die-halves that are self-aligning, as constructed according to the principles of the present invention.

Referring now to FIG. 46, a two-die (or mold) system is illustrated, in which the top die- or mold-half 500 is positioned above the bottom die- or mold-half 510, with a planar layer or film of material 530 positioned therebetween. The bottom mold- or die-half 510 includes a top substantially planar surface 518 from which protrudes a number of projections 512. Each of these projections has a "left" face 514 and a "right" face 516 (as seen in FIG. 46) and these two faces come to a point at 520. The top mold- or die-half 500 includes several recess areas 502, each one having a "left" face 504 and a "right" face 506 (as seen in FIG. 46), and also a bottom substantially planar surface 508.

The film 530 includes a bottom planar surface 534 and a top planar surface 532. In general, the film preferably is heated so that it becomes relatively soft and will easily melt and flow when under pressure at this temperature. Up until that point, however, the film 530 is not heated to a point where it will become deformed due to gravity alone.

Figure 47:
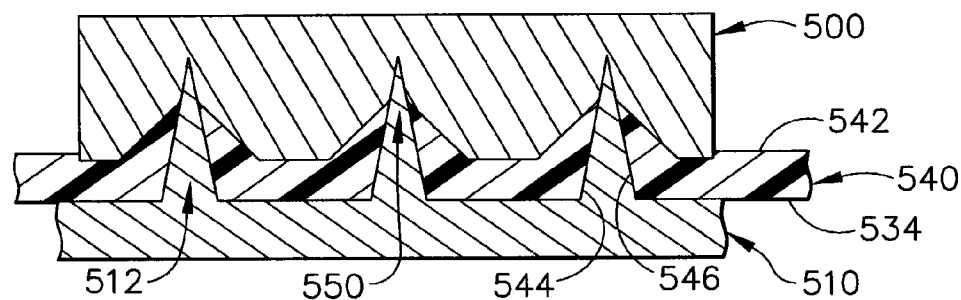

FIG. 47 illustrates the next step of the construction process, and the top mold/die-half 500 and the bottom mold/die-half 510 have been brought together such that the plastic film has been squeezed and molded into its final shape. In this situation, the plastic film is now generally designated by the reference numeral 540, and its top surface is illustrated at 542. Each of the projections 512 now protrudes all the way through the film 540 and into the recess area 502 of the top mold/die-half 500. This will form a pyramidal microelement with a microhole or opening at 550, which is better seen in FIG. 48. The microhole 550 is formed from a channel that exists in FIG. 47 between a surface 544 and a surface 546 in the film 540. When the die- or mold-halves are cooled and then released, the plastic film structure 540 is separated from the die/mold-halves, thereby creating the microstructure 540 seen in FIG. 48. The top surface of the substrate is illustrated at 542, each of the four-sided pyramidal microelements has a "left" face 552 and a "right" face 554 (as seen in FIG. 48) and has an opening or a through-hole 550 near or at the peak of the pyramid.

Figure 48:
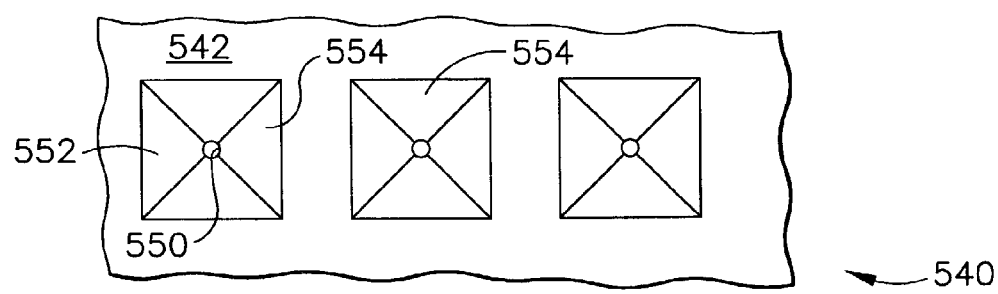

One important feature of the design illustrated in FIGS. 46-48 is that the two die-halves or mold-halves 500 and 510 are essentially self-aligning within a certain tolerance. In other words, one of the die/mold-halves can be held in place in the horizontal direction (as seen in these views) while the other, opposite die/mold-half can be allowed to "float" to a certain degree in that same horizontal direction. When the two halves 500 and 510 are brought together in the transition from the positions illustrated in FIGS. 46 to 47, the shapes of the projections 512 and of the recesses 502 will be such that, if somewhat not perfectly aligned, they will tend to become aligned as the two halves 510, 510 are brought together, because the points 520 will slide up either of the side-wall surfaces 504 or 506. This will allow the construction of the microstructures 540 to be accomplished with great precision, without the need for extreme precision in the actual positioning of the die/mold-halves 500 and 510. Of course, the tolerance must be tight enough that the points 520 of the bottom die/mold-half 510 will come within the perimeter of the open areas 502 of the top die/mold-half 500.

Figure 49:
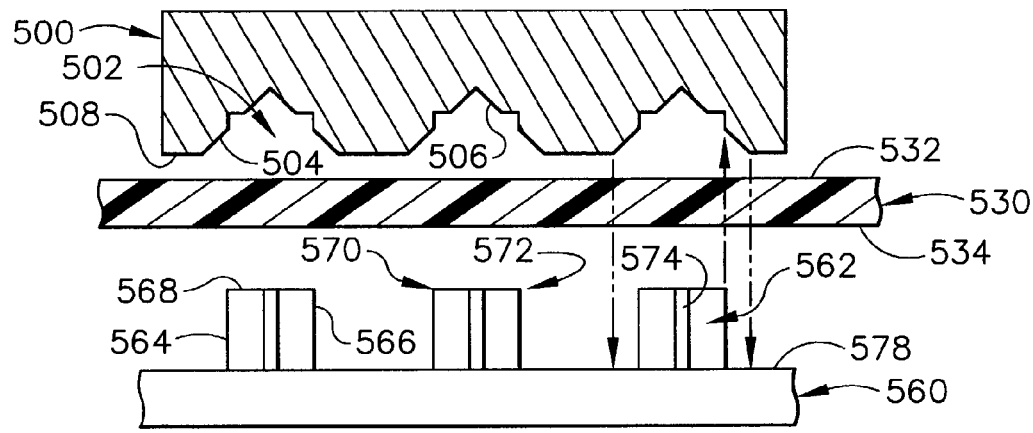
FIGS. 49-52 show the process steps in forming a set of well-aligned microelements on a microstructure, using two mold/die-halves that are self-aligning, as constructed according to the principles of the present invention.
Figure 50:
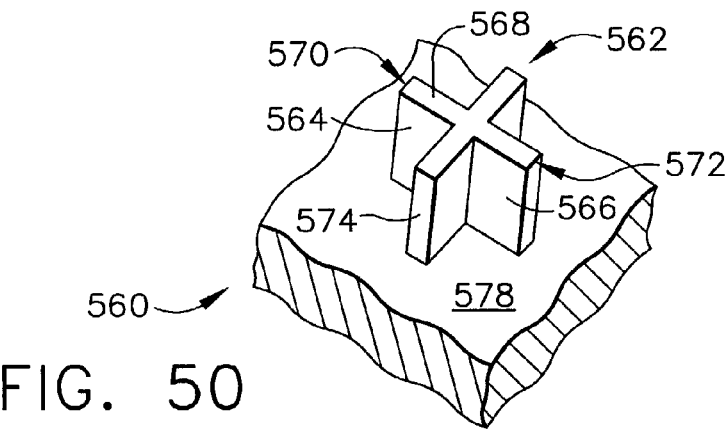

FIG. 49 illustrates another set of die/mold-halves 500 and 560, which are used to squeeze a thin layer or film of material 530 into a set of microelements. The top die- or mold-half 500 again exhibits a number of open areas or spaces 502, each having a "left" sloped wall 504 and a "right" sloped wall 506 (as seen on FIG. 49). The bottom mold- or die-half 560 exhibits a number of protrusions or elevated structures 562 that sit on or protrude from the top surface 578 of the substrate, which has a bottom planar surface. Each of these mold elements 562 includes a "left" wall 564, a "right" wall 566, and a "top" surface 568 (as seen on FIG. 49). There is also a "near" surface 574 and two top edges 570 and 572, again as seen on FIG. 49. A perspective view of one of these mold elements 562 is illustrated in FIG. 50. It can be seen in FIG. 50 that this protrusion 562 is formed in the shape of a plus sign (+), and the "left" wall 564 has an opposing "right" wall 566, and also the "near" wall 574 can be seen, all projecting from the top substrate 578 of the bottom die- or mold-half 560. The two top edges 570 and 572 also can easily be seen in FIG. 50.

As in the procedure illustrated in FIGS. 46-48, the film 530 exhibits a top planar surface 532 and a bottom planar surface 534, and preferably is heated before being pressed by the top and bottom mold- or die-halves 500 and 560. The proper temperature that the film is heated to should allow the material of the film 530 to easily melt and flow when under pressure. Until that step, however, the film 530 is not heated to a point where it will become deformed due to gravity alone.

Figure 51:
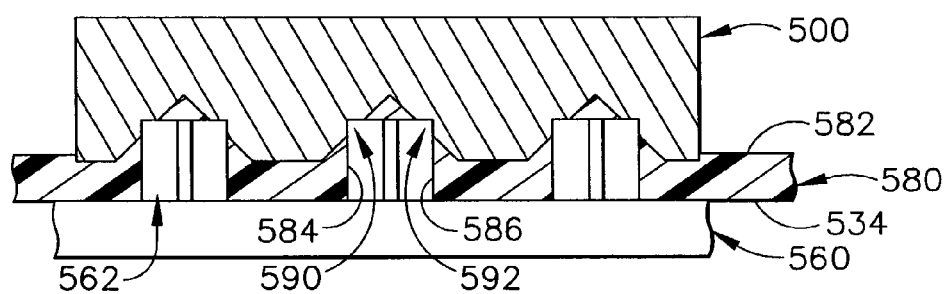
Figure 52:
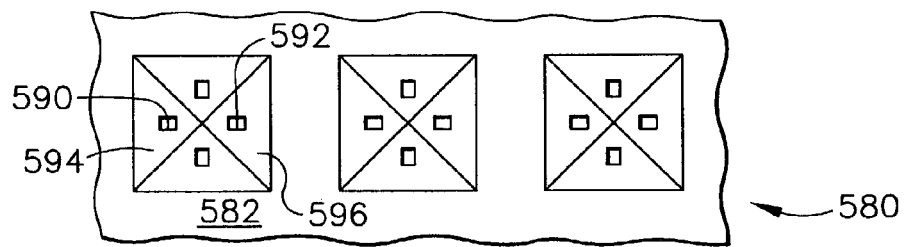

FIG. 51 illustrates the arrangement when the two mold/die-halves 500 and 560 are squeezed together with the film 580 therebetween, and the top surface of the film 582 becomes pressed into an array of microelements, which also can be viewed in FIG. 52. In FIG. 51, each microelement will have an internal "left" wall 584 and an internal "right" wall 586 (as seen in FIG. 51). These wall structures 584 and 586 will project upward until meeting the top surface 582 of the film 580, at which point openings will be formed at 590 and 592. These openings can be seen in the final product, as viewed on FIG. 52.

The mold- or die-halves will be cooled and then separated, and the film 580 will also become separated and forms a microstructure that consists of an array of microelements that, in FIG. 52, have the appearance of a four-sided pyramid, each having microholes or openings. The four-sided pyramids are formed from the top substrate 582, and each microelement pyramid has a "left" sloped wall 594 and a "right" sloped wall 596 (as seen on FIG. 52). The sloped wall 594 has an opening or through-hole 590 while the sloped wall 596 has an opening or through-hole 592. Of course, different shapes could be formed and each shape could have only a single through-hole, or multiple through-holes as seen on FIG. 52, without departing from the principles of the present invention. The two mold- or die-halves 500 and 560 are also somewhat self-aligning, and only one of these halves 500, 560 need necessarily be held firmly in place in the horizontal direction (as seen in FIG. 49), while the other half can be allowed to "float" to a small extent in the same horizontal direction. So long as the upper edges 570 and 572 of each projection of the bottom mold/die-half 560 will extend within the open area 502 of the top die/mold-half 500, then precise alignment of bottom die/ mold-half 560 need not be maintained. Of course, the horizontal tolerance itself will be fairly tight after all, since the structures being formed are themselves quite small, which is why they are referred to as microelements.

Figure 53:
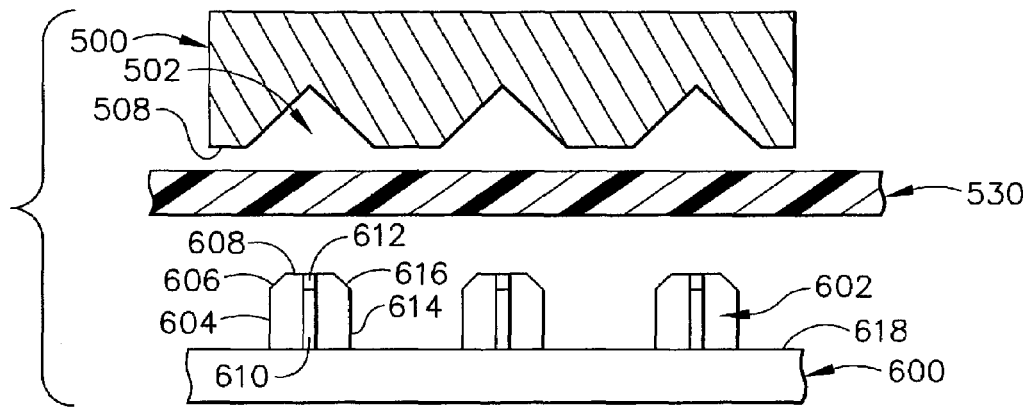
FIGS. 53-56 show the process steps in forming a set of well-aligned microelements in a microstructure (in which the microelements have a somewhat different shape), using two mold/die-halves that are self-aligning, as constructed according to the principles of the present invention.
Figure 54:
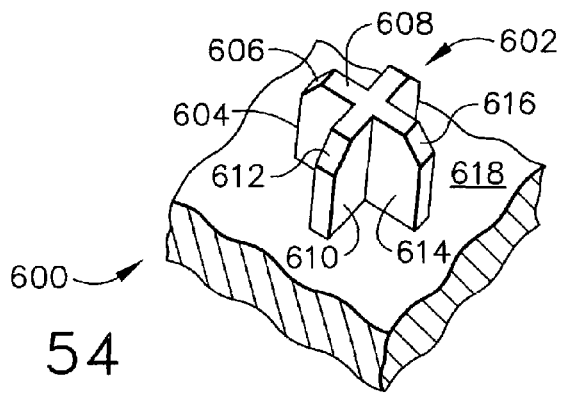

FIGS. 53-56 illustrate a variation of the structures that were described above in reference to FIGS. 49-52. Referring now to FIG. 53, the bottom mold- or die-half, generally indicated by the reference numeral 600, exhibits another set of protrusions that have the appearance of a plus sign, however, these protrusions are not brought to the same upper edges. Instead, each of the upward projecting members has a chamfer-type effect, in that there is a 45° angle sloped face between the horizontal face and the vertical face. More specifically, along the "left" projection surface 604 (as seen on FIG. 53), this vertical face terminates at an angular face 606 before meeting a horizontal face 608. The same sort of physical shape is exhibited in the "right" side face 614 (as seen in FIG. 53), which projects vertically upward to an angled face 616 before arriving at the horizontal face 608 at the top. There is also a "near" face 610 (as seen on FIG. 53) that travels upward in a near-vertical direction until meeting an angular face 612. These faces are better viewed in a perspective view of FIG. 54.

The overall bottom die- or mold-half 600 exhibits a top planar surface 618, and each of the upper projections as an element of the micromold 600 are generally indicated by the reference numeral 602. Each of these projections 602 is designed to fit within the open space 502 of the top die/mold-half 500, in a similar manner to that described on FIG. 49 with respect to the upward projections 562.

Figure 55:
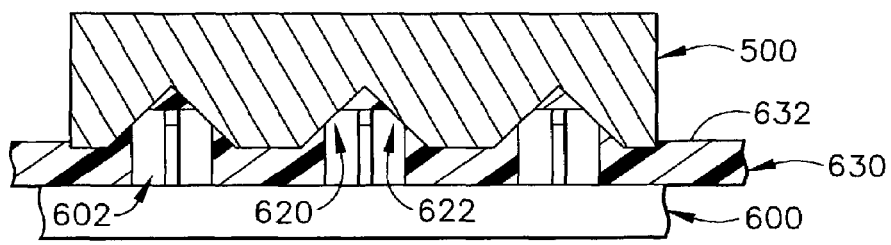

After the material 530 is heated to a temperature that will allow the material to fairly easily melt and flow when under pressure, the two mold/die-halves 500 and 600 are squeezed together, as illustrated on FIG. 55. Each of the projections 602 will cause openings to be formed in the top surface 632 of the film material 630, generally at the locations 620 and 622. This is better seen in FIG. 56 which shows the final result 630 after the mold/die-halves 500 and 600 have been cooled and separated.

Figure 56:
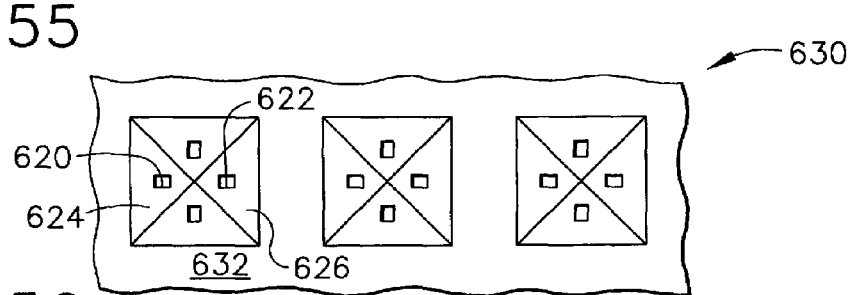

In FIG. 56, it can be seen that an array of individual microelements has been formed in the top surface 632 of the microstructure 630. In this illustration, each of the microelements is shaped as a four-sided pyramid, each having a "left" sloped face 624 and a "right" sloped face 626 (as seen on FIG. 56). The sloped face 624 exhibits an opening or through-hole 620, while the sloped face 626 has an opening or through-hole 622 (e.g., microholes).

As in earlier examples, the die/mold-halves 500 and 600 are somewhat self-aligning, so that either one of the halves 500, 600 can be held precisely in place in the horizontal direction (as seen in FIG. 53) while the other such half can be allowed to "float" to a certain tolerance in the same horizontal direction. So long as the upper surfaces of each of the projections 602 fall within the open area 502 in the top half 500, the two mold/die-halves should be sufficiently self-aligning to allow a small tolerance to exist between their exact positions, while forming parts to a high degree of accuracy.

It will be understood that the exact shapes of the projections of the bottom die/mold-halves can vary from those illustrated in FIGS. 46-56, without departing from the principles of the present invention.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed is:

1. A method for constructing a microstructure, said method comprising:
    (a) providing a substrate of a first material, said substrate having a first substantially planar surface and a second substantially planar surface opposite said first surface, said substrate having a plurality of openings in the form of through-holes formed between said first and second surfaces; and then
    (b) pressing against the first surface of said substrate of material with an object having a predetermined shape to thereby form a plurality of permanent microelement protrusions in said first surface, said plurality of microelement protrusions being of at least one predetermined shape and size, each of said plurality of microelement protrusions having a base-shape that forms a perimeter along said first surface;
    wherein at least one of said plurality of microelement protrusions exhibit at least one of said plurality of openings within their said perimeter, and said microelement protrusions are suitable for penetrating the stratum corneum of human skin.

2. The method as recited in claim 1, wherein a location of said plurality of openings in said substrate is one of: (a) well-aligned with respect to the perimeters of said plurality of microelement protrusions, such that at least one of said plurality of openings fall within at least one of said perimeters; and (b) semi-random, such that a number and density of spacing of said plurality of openings is sufficient so that at least one of said plurality of microelement protrusions exhibits at least one of said openings, even though many of said openings will not fall within at least one of said perimeters.

3. The method as recited in claim 1, wherein at least one of said plurality of openings are not completely closed by said pressing operation.

4. The method as recited in claim 1, wherein said step (b) of pressing against said substrate comprises one of: embossing; molding; punching; squeezing; and stamping.

5. A method for constructing a microstructure, said method comprising the steps of:
    (a) providing a substrate of a first material, said substrate having a first substantially planar surface and a second substantially planar surface opposite said first surface, said substrate having a plurality of openings in the form of through-holes formed between said first and second surfaces; then
    (b) pressing against the first surface of said substrate of material with an object having a predetermined shape to thereby form a plurality of microelement protrusions in said first surface, said plurality of microelement protrusions being of at least one predetermined shape and size, each of said plurality of microelement protrusions having a base-shape that forms a perimeter along said first surface; wherein at least one of said plurality of microelement protrusions exhibit at least one of said plurality of openings within their said perimeter, and said microelement protrusions are suitable for penetrating the stratum corneum of human skin (c) before said pressing step (b), placing a second material into at least one of said plurality of openings, said second material having at least one property that is different from at least one property of said first material; and (d) after said pressing step (b), removing said second material from at least one of said plurality of openings.

6. The method as recited in claim 5, wherein said step (c) of placing a second material into at least one of said plurality of openings comprises one of: (i) passing said substrate of a first material through a bath of said second material at a raised temperature, such that said second material readily flows into said plurality of openings; and (ii) co-extruding said second material onto said substrate of a first material.

7. The method as recited in claim 5, wherein said step (d) of removing the second material comprises one of: raising a temperature to above a melting point of said second material; applying a chemical that dissolves said second material but not said first material; applying a chemical that reacts with said second material but not said first material; mechanically punching said second material from said plurality of openings; and mechanically drilling said second material from said plurality of openings.

8. The method as recited in claim 1, wherein the substrate comprises polymethymethacrylate or polysulfone.

9. The method as recited in claim 5, wherein a location of said plurality of openings in said substrate is one of: (a) well-aligned with respect to the perimeters of said plurality of microelement protrusions, such that at least one of said plurality of openings fall within at least one of said perimeters; and (b) semi-random, such that a number and density of spacing of said plurality of openings is sufficient so that at least one of said plurality of microelement protrusions exhibits at least one of said openings, even though many of said openings will not fall within at least one of said perimeters.

10. The method as recited in claim 5, wherein said step of pressing against said substrate comprises one of: embossing; molding; punching; squeezing; and stamping.

* * * * *

UNITED STATES PATENT AND TRADEMARK OFFICE
CERTIFICATE OF CORRECTION

PATENT NO. : 7,578,954 B2  Page 1 of 1
APPLICATION NO. : 10/373251
DATED : August 25, 2009
INVENTOR(S) : Gartstein et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 368 days.

Signed and Sealed this

Fourteenth Day of September, 2010

David J. Kappos
*Director of the United States Patent and Trademark Office*